(12) United States Patent
Collingwood et al.

(10) Patent No.: US 8,664,228 B2
(45) Date of Patent: Mar. 4, 2014

(54) 3,5-DIAMINO-6-CHLORO-PYRAZINE-2-CARBOXYLIC ACID DERIVATIVES AND THEIR USE AS EPITHELIAL SODIUM CHANNEL BLOCKERS FOR THE TREATMENT OF AIRWAY DISEASES

(75) Inventors: Stephen Paul Collingwood, Horsham (GB); Catherine Howsham, Horsham (GB); Thomas Anthony Hunt, Horsham (GB)

(73) Assignee: Novartis AG, Basel (CH)

( * ) Notice: Subject to any disclaimer, the term of this patent is extended or adjusted under 35 U.S.C. 154(b) by 84 days.

(21) Appl. No.: 12/990,905

(22) PCT Filed: May 11, 2009

(86) PCT No.: PCT/EP2009/055657
§ 371 (c)(1),
(2), (4) Date: Nov. 3, 2010

(87) PCT Pub. No.: WO2009/138378
PCT Pub. Date: Nov. 19, 2009

(65) Prior Publication Data
US 2011/0059989 A1     Mar. 10, 2011

(30) Foreign Application Priority Data
May 13, 2008 (EP) .................... 08156060

(51) Int. Cl.
*A61K 31/4965* (2006.01)
(52) U.S. Cl.
USPC ..................... 514/255.06; 544/407
(58) Field of Classification Search
USPC ....................................... 544/407
See application file for complete search history.

(56) References Cited

U.S. PATENT DOCUMENTS 4,550,111 A * 10/1985 Barlow et al. ............ 514/255.06
4,803,206 A *  2/1989 Magatti et al. ........... 514/255.06

FOREIGN PATENT DOCUMENTS

WO    WO2005/025496    3/2005
WO    WO2006/023573    3/2006

OTHER PUBLICATIONS

Li et al. Structure-activity relationship of amiloride analogs as blockers of epithelial sodium channels. 1987, Journal of Membrane Biology, 95, 171-185.*
Jack Li et al., "Stereoselective Blockade of Amphibian Epithelial Sodium Channels by Amiloride Analogs" *J. Pharmcology and Experimental Therapeutics* 267(3):1081-1084, Dec. 1, 1993.
Thomas Russ et al., "Preparation and Diuretic Properties of Novel Amiloride Analogues" *Arch. Pharm.* 325:761-767, Dec. 12, 1992.

* cited by examiner

*Primary Examiner* — Brian McDowell
(74) *Attorney, Agent, or Firm* — Mark W. Milstead

(57) ABSTRACT

A compound of Formula I

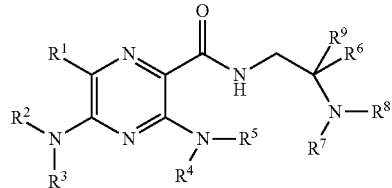

in free or salt or solvate form, where $R^1$, $R^2$, $R^3$, $R^4$, $R^5$, $R^6$, $R^7$, $R^8$ and $R^9$ have the meanings as indicated in the specification, is useful for treating diseases which respond to the blockade of the epithelial sodium channel. Pharmaceutical compositions that contain the compounds and processes for preparing the compounds are also described.

3 Claims, No Drawings

3,5-DIAMINO-6-CHLORO-PYRAZINE-2-CARBOXYLIC ACID DERIVATIVES AND THEIR USE AS EPITHELIAL SODIUM CHANNEL BLOCKERS FOR THE TREATMENT OF AIRWAY DISEASES

This application is a U.S. National Phase filing of International Application No. PCT/EP2009/055657 filed 11 May 2009 and claims priority to European Patent Application No. 08156060.9 filed 13 May 2008, the contents of which are incorporated herein by reference in their entirety, This invention relates to organic compounds, their preparation and use as pharmaceuticals.

In one aspect, the invention provides compounds according to Formula I:

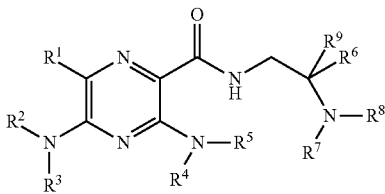

or solvates, hydrates or pharmaceutically acceptable salts thereof, wherein $R^1$ is halogen;

$R^2$, $R^3$, $R^4$ and $R^5$ are each independently selected from H and $C_1$-$C_6$ alkyl;

$R^6$ is —($C_0$-$C_6$ alkylene)-$R^{10}$, wherein the alkylene linker is optionally substituted by one or more groups selected from $C_1$-$C_3$ alkyl, halo and OH, provided that when the alkylene linker is absent, $R^{10}$ is other than H;

$R^7$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl and —($C_1$-$C_3$ alkylene)-aryl, wherein the cycloalkyl and aryl groups are each optionally substituted by one or more substituents selected from List Z;

$R^8$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl, aryl, heteroaryl, heterocyclyl, and a group of the formula A-B, wherein the aryl, heteroaryl and heterocyclyl groups are each optionally substituted by one or more substituents selected from List Z; or $R^7$ and $R^8$, together with the nitrogen atom to which they are attached form a 4- to 10-membered nitrogen-containing heterocyclic group which is optionally substituted by one or more substituents selected from the List Z; or $R^6$ and $R^8$, together with the atoms to which they are attached form a 4- to 10-membered nitrogen-containing heterocyclic group which is optionally substituted by one or more substituents selected from the List Z;

A is a bond, —C(=NH)NH—, —($CH_2$)$_d$-D-($CH_2$)$_b$— or —C(=NH)NH—($CH_2$)$_d$-D-($CH_2$)$_b$—;

B is selected from H, $C_1$-$C_6$ alkyl, —($C_0$-$C_4$ alkylene)-$C_3$-$C_{10}$ cycloalkyl, $C_5$-$C_{10}$ cycloalkenyl, —($C_0$-$C_4$ alkylene)-aryl, —($C_0$-$C_4$ alkylene)-heteroaryl and —($C_0$-$C_4$ alkylene)-heterocyclyl, wherein the aryl, heteroaryl and heterocyclyl groups are each optionally substituted by one or more substituents selected from List Z;

D is selected from a bond, —O—, —C(O)—, —C(O)NH—, —C(O)O—, —OC(O)—, —NHC(=N)NH—, —S($O_2$)—, —S($O_2$)NH—, —NHC(O)—, —NHC(O)O—, —OC(O)NH—, —NHS($O_2$)—, —NHC(O)NH— and —NH—;

d is 1, 2 or 3;

b is 0, 1, 2 or 3;

y is 1, 2 or 3;

$R^9$ is H or $C_1$-$C_6$ alkyl; or $R^6$ and $R^9$, together with the carbon atom to which they are attached, form a $C_3$-$C_{10}$ cycloalkyl group, a $C_5$-$C_{10}$ cycloalkenyl group or a 4- to 10-membered heterocyclyl group, wherein each of the ring systems is optionally substituted by one or more substituents selected from the List Z;

$R^{10}$ is selected from H, $C_3$-$C_{10}$ cycloalkyl, $C_5$-$C_{10}$ cycloalkenyl, $NR^{11}R^{12}$, $C(O)NR^{13}R^{14}$, aryl, heteroaryl, heterocyclyl and a group of the formula P—($CH_2$)$_m$-Q, wherein each of the ring systems is optionally substituted by one or more substituents selected from the List Z;

P is selected from a bond, —O—, —C(O)—, —C(O)NH—, —C(O)O—, —OC(O)—, —NHC(=N)NH—, —S($O_2$)—, —S($O_2$)NH—, —NHC(O)—, —NHC(O)O—, —OC(O)NH—, —NHS($O_2$)—, —NHC(O)NH— and —NH—;

Q is selected from H, $C_1$-$C_6$ alkyl, $C_3$-$C_{10}$ cycloalkyl, $C_5$-$C_{10}$ cycloalkenyl, aryl, heteroaryl and heterocyclyl, wherein the aryl, heteroaryl and heterocyclyl groups are each optionally substituted by one or more substituents selected from List Z;

m is 0, 1, 2 or 3;

$R^{11}$ is selected from H, $C_1$-$C_6$ alkyl, $C_3$-$C_{10}$ cycloalkyl, $C_5$-$C_{10}$ cycloalkenyl and —($C_1$-$C_3$ alkylene)-$C_3$-$C_{10}$ cycloalkyl;

$R^{12}$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl, —C(O)$C_1$-$C_6$ alkyl, —C(O)$C_3$-$C_{10}$ cycloalkyl, —C(O)($C_1$-$C_3$ alkylene)-$C_3$-$C_{10}$ cycloalkyl, —C(O)($CH_2$)$_x$ aryl, —C(O)($CH_2$)$_x$ heteroaryl, —C(O)($CH_2$)$_x$ heterocyclyl, —C(O)Oalkyl, C(O)Oaryl, ($CH_2$)$_x$ aryl, ($CH_2$)$_x$ heteroaryl and —($CH_2$)$_x$ heterocyclyl, wherein each of the ring systems is optionally substituted by one or more substituents selected from the List Z;

$R^{13}$ is selected from H, $C_1$-$C_6$ alkyl, $C_3$-$C_{10}$ cycloalkyl, $C_5$-$C_{10}$ cycloalkenyl and —($C_1$-$C_3$ alkylene)-$C_3$-$C_{10}$ cycloalkyl;

$R^{14}$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl, —($CH_2$)$_z$ aryl, ($CH_2$)$_z$ heteroaryl and ($CH_2$)$_z$ heterocyclyl, wherein each of the ring systems is optionally substituted by one or more substituents selected from the List Z;

x is 0, 1, 2 or 3;

z is 0, 1, 2 or 3;

Z is independently selected from OH, aryl, heteroaryl, heterocyclyl, benzyl, $C_1$-$C_6$ alkyl optionally substituted by one or more halogen atoms or OH groups, $C_1$-$C_6$ alkoxy optionally substituted by one or more halogen atoms or OH groups, —Oaryl, —Obenzyl, —O($CH_2$)$_a$C(O)E, $NR^{15}$($SO_2$)$R^{17}$, ($SO_2$)$NR^{15}R^{16}$, ($SO_2$)$R^{17}$, $NR^{15}C(O)R^{17}$, C(O)$NR^{15}R^{17}$, $NR^{15}C(O)NR^{16}R^{17}$, $NR^{15}C(O)OR^{17}$, OC(O)$NR^{15}R^{17}$, $NR^{15}R^{17}$, C(O)$OR^5$, OC(O)$R^{15}$, C(O)$R^{17}$, $SR^{15}$, CN, $NO_2$, and halogen;

a is 0, 1, 2, 3 or 4, where the alkylene group is optionally substituted by OH or $NH_2$ when a is 1, 2, 3 or 4;

E is $NR^{15}R^{17}$ or $OR^{17}$;

each $R^{15}$ and $R^{16}$ are independently selected from H, $C_1$-$C_6$ alkyl, $C_3$-$C_{10}$ cycloalkyl, $C_5$-$C_{10}$ cycloalkenyl and —($C_1$-$C_3$ alkylene)-$C_3$-$C_{10}$ cycloalkyl; and each $R^{17}$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl, $C_5$-$C_{10}$ cycloalkenyl, aryl, heteroaryl, heterocyclyl, where each of the ring systems is optionally substituted by OH, halo, $C_1$-$C_3$ alkyl and $C_1$-$C_3$ alkoxy, provided that $R^6$ is not benzyl when $R^7$, $R^8$ and $R^9$ are all hydrogen.

In an embodiment of the invention, there is provided a compound according to the Formula Ia:

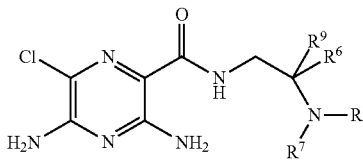

Ia or solvates, hydrates or pharmaceutically acceptable salts thereof, wherein $R^6$ is —($C_0$-$C_6$ alkylene)-$R^{10}$, wherein the alkylene linker is optionally substituted by one or more groups selected from $C_1$-$C_3$ alkyl, halo and OH, provided that when the alkylene linker is absent, $R^{10}$ is other than H;

$R^7$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl and —($C_1$-$C_3$ alkylene)-aryl, wherein the cycloalkyl and aryl groups are each optionally substituted by one or more substituents selected from List Z;

$R^8$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl, aryl, heteroaryl, heterocyclyl, and a group of the formula A-B, wherein the aryl, heteroaryl and heterocyclyl groups are each optionally substituted by one or more substituents selected from List Z; or $R^7$ and $R^8$, together with the nitrogen atom to which they are attached form a 4- to 10-membered nitrogen-containing heterocyclic group which is optionally substituted by one or more substituents selected from the List Z; or $R^6$ and $R^8$, together with the atoms to which they are attached form a 4- to 10-membered nitrogen-containing heterocyclic group which is optionally substituted by one or more substituents selected from the List Z;

A is a bond, —C(=NH)NH—, —($CH_2$)$_d$-D-($CH_2$)$_b$— or —C(=NH)NH—($CH_2$)$_d$-D-($CH_2$)$_b$—;

B is selected from H, $C_1$-$C_6$ alkyl, —($C_0$-$C_4$ alkylene)-$C_3$-$C_{10}$ cycloalkyl, $C_5$-$C_{10}$ cycloalkenyl, —($C_0$-$C_4$ alkylene)-aryl, —($C_0$-$C_4$ alkylene)-heteroaryl and —($C_0$-$C_4$ alkylene)-heterocyclyl, wherein the aryl, heteroaryl and heterocyclyl groups are each optionally substituted by one or more substituents selected from List Z;

D is selected from a bond, —O—, —C(O)—, —C(O)NH—, —C(O)O—, —OC(O)—, —NHC(=N)NH—, —S($O_2$)—, —S($O_2$)NH—, —NHC(O)—, —NHC(O)O—, —OC(O)NH—, —NHS($O_2$)—, —NHC(O)NH— and —NH—;

d is 1, 2 or 3;

b is 0, 1, 2 or 3;

y is 1, 2 or 3;

$R^9$ is H or $C_1$-$C_6$ alkyl; or $R^6$ and $R^9$, together with the carbon atom to which they are attached, form a $C_3$-$C_{10}$ cycloalkyl group, a $C_5$-$C_{10}$ cycloalkenyl group or a 4- to 10-membered heterocyclyl group, wherein each of the ring systems is optionally substituted by one or more substituents selected from the List Z;

$R^{10}$ is selected from H, $C_3$-$C_{10}$ cycloalkyl, $C_5$-$C_{10}$ cycloalkenyl, $NR^{11}R^{12}$, $C(O)NR^{13}R^{14}$, aryl, heteroaryl, heterocyclyl and a group of the formula P—($CH_2$)$_m$-Q, wherein each of the ring systems is optionally substituted by one or more substituents selected from the List Z;

P is selected from a bond, —O—, —C(O)—, —C(O)NH—, —C(O)O—, —OC(O)—, —NHC(=N)NH—, —S($O_2$)—, —S($O_2$)NH—, —NHC(O)—, —NHC(O)O—, —OC(O)NH—, —NHS($O_2$)—, —NHC(O)NH— and —NH—;

Q is selected from H, $C_1$-$C_6$ alkyl, $C_3$-$C_{10}$ cycloalkyl, $C_5$-$C_{10}$ cycloalkenyl, aryl, heteroaryl and heterocyclyl, wherein the aryl, heteroaryl and heterocyclyl groups are each optionally substituted by one or more substituents selected from List Z;

m is 0, 1, 2 or 3;

$R^{11}$ is selected from H, $C_1$-$C_6$ alkyl, $C_3$-$C_{10}$ cycloalkyl, $C_5$-$C_{10}$ cycloalkenyl and —($C_1$-$C_3$ alkylene)-$C_3$-$C_{10}$ cycloalkyl;

$R^{12}$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl, —C(O)$C_1$-$C_6$ alkyl, —C(O)$C_3$-$C_{10}$ cycloalkyl, —C(O)($C_1$-$C_3$ alkylene)-$C_3$-$C_{10}$ cycloalkyl, —C(O)($CH_2$)$_x$ aryl, —C(O)($CH_2$)$_x$ heteroaryl, —C(O)($CH_2$)$_x$ heterocyclyl, —C(O)Oalkyl, C(O)Oaryl, ($CH_2$)$_x$ aryl, ($CH_2$)$_x$ heteroaryl and —($CH_2$)$_x$ heterocyclyl, wherein each of the ring systems is optionally substituted by one or more substituents selected from the List Z;

$R^{13}$ is selected from H, $C_1$-$C_6$ alkyl, $C_3$-$C_{10}$ cycloalkyl, $C_5$-$C_{10}$ cycloalkenyl and —($C_1$-$C_3$ alkylene)-$C_3$-$C_{10}$ cycloalkyl;

$R^{14}$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl, —($CH_2$)$_z$ aryl, ($CH_2$)$_z$ heteroaryl and ($CH_2$)$_z$ heterocyclyl, wherein each of the ring systems is optionally substituted by one or more substituents selected from the List Z;

x is 0, 1, 2 or 3;

z is 0, 1, 2 or 3;

Z is independently selected from OH, aryl, heteroaryl, heterocyclyl, benzyl, $C_1$-$C_6$ alkyl optionally substituted by one or more halogen atoms or OH groups, $C_1$-$C_6$ alkoxy optionally substituted by one or more halogen atoms or OH groups, —Oaryl, —Obenzyl, —O($CH_2$)$_a$C(O)E, $NR^{15}$($SO_2$)$R^{17}$, ($SO_2$)$NR^{15}R^{16}$, ($SO_2$)$R^{17}$, $NR^{15}C(O)R^{17}$, C(O)$NR^{15}R^{17}$, $NR^{15}C(O)NR^{16}R^{17}$, $NR^{15}C(O)OR^{17}$, OC(O)$NR^{15}R^{17}$, $NR^{15}R^{17}$, C(O)$OR^{15}$, OC(O)$R^{15}$, C(O)$R^{17}$, $SR^{15}$, CN, $NO_2$, and halogen;

a is 0, 1, 2, 3 or 4, where the alkylene group is optionally substituted by OH or $NH_2$ when a is 1, 2, 3 or 4;

E is $NR^{15}R^{17}$ or $OR^{17}$;

each $R^{15}$ and $R^{16}$ are independently selected from H, $C_1$-$C_6$ alkyl, $C_3$-$C_{10}$ cycloalkyl, $C_5$-$C_{10}$ cycloalkenyl and —($C_1$-$C_3$ alkylene)-$C_3$-$C_{10}$ cycloalkyl; and each $R^{17}$ is selected from H, $C_1$-$C_6$ alkyl, $C_3$-$C_{10}$ cycloalkyl, $C_5$-$C_{10}$ cycloalkenyl, —($C_1$-$C_3$ alkylene)-$C_3$-$C_{10}$ cycloalkyl, $C_5$-$C_{10}$ cycloalkenyl, aryl, heteroaryl, heterocyclyl, where each of the ring systems is optionally substituted by OH, halo, $C_1$-$C_3$ alkyl and $C_1$-$C_3$ alkoxy, provided that $R^6$ is not benzyl when $R^7$, $R^8$ and $R^9$ are all hydrogen.

In a still further embodiment of the invention as defined anywhere above, $R^9$ is H.

In a further embodiment, A is a bond, —C(=NH)NH— or —($CH_2$)$_d$-D-($CH_2$)$_b$—.

In a yet further embodiment of the invention as defined anywhere above, $R^7$ is H or $C_1$-$C_3$ alkyl; and
$R^8$ is H; or
$R^6$ and $R^8$, together with the atoms to which they are attached form a 5- or 6-membered nitrogen-containing heterocyclic group which is optionally substituted by one or more substituents selected from the List Z.

In a further embodiment of the invention as defined anywhere above, $R^{10}$ is H, $NHR^{12}$, $C(O)NHR^{14}$, phenyl or a $C_5$-$C_6$ cycloalkyl group;
$R^{12}$ is selected from H, $C_1$-$C_6$ alkyl, —$C(O)C_1$-$C_6$ alkyl, —$C(O)(CH_2)_x$ phenyl and $(CH_2)_x$ phenyl, wherein each of the phenyl groups is optionally substituted by one or more substituents selected from the List Z;
$R^{14}$ is selected from H, $C_1$-$C_6$ alkyl and —$(CH_2)_z$ aryl, wherein each of the phenyl groups is optionally substituted by one or more substituents selected from the List Z;
x is 0, 1, 2 or 3; and
z is 0, 1, 2 or 3.

Optionally, when $R^6$ is Me, $R^9$ is other than Me. Suitably, when $R^6$ is Me, $R^9$ is other than H or Me.

In a yet further embodiment of the invention as defined anywhere above, there is provided a compound according to Formula I selected from:
3,5-Diamino-6-chloro-pyrazine-2-carboxylic acid ((R)-1-ethyl-pyrrolidin-2-ylmethyl)-amide,
3,5-Diamino-6-chloro-pyrazine-2-carboxylic acid [2-amino-5-(4-methoxy-phenyl)-pentyl]-amide,
3,5-Diamino-6-chloro-pyrazine-2-carboxylic acid [5-[4-((S)-2,3-dihydroxy-propoxy)-phenyl]-2-(2,4-dimethoxy-benzylamino)-pentyl]-amide,
3,5-Diamino-6-chloro-pyrazine-2-carboxylic acid ((S)-2-amino-pentyl)-amide,
3,5-Diamino-6-chloro-pyrazine-2-carboxylic acid ((R)-2-amino-pentyl)-amide,
3,5-Diamino-6-chloro-pyrazine-2-carboxylic acid ((S)-2-amino-3-cyclohexyl-propyl)-amide,
3,5-Diamino-6-chloro-pyrazine-2-carboxylic acid ((S)-2-amino-3-methyl-butyl)-amide,
3,5-Diamino-6-chloro-pyrazine-2-carboxylic acid ((S)-2-amino-4-methyl-pentyl)-amide,
3,5-Diamino-6-chloro-pyrazine-2-carboxylic acid ((S)-1-pyrrolidin-2-ylmethyl)-amide,
3,5-Diamino-6-chloro-pyrazine-2-carboxylic acid ((R)-1-piperidin-2-ylmethyl)-amide,
3,5-Diamino-6-chloro-pyrazine-2-carboxylic acid (1-amino-cyclopentylmethyl)-amide,
3,5-Diamino-6-chloro-pyrazine-2-carboxylic acid {(S)-2-amino-6-[3-(4-benzyloxy-phenyl)-propionylamino]-hexyl}-amide,
3,5-Diamino-6-chloro-pyrazine-2-carboxylic acid ((S)-2-amino-hexyl)-amide,
3,5-Diamino-6-chloro-pyrazine-2-carboxylic acid ((R)-2-amino-butyl)-amide,
3,5-Diamino-6-chloro-pyrazine-2-carboxylic acid ((R)-2-amino-propyl)-amide,
3,5-Diamino-6-chloro-pyrazine-2-carboxylic acid ((S)-2-amino-butyl)-amide,
3,5-Diamino-6-chloro-pyrazine-2-carboxylic acid ((S)-2-amino-propyl)-amide,
3,5-Diamino-6-chloro-pyrazine-2-carboxylic acid ((S)-1-piperidin-2-ylmethyl)-amide,
3,5-Diamino-6-chloro-pyrazine-2-carboxylic acid ((R)-1-pyrrolidin-2-ylmethyl)-amide,
3,5-Diamino-6-chloro-pyrazine-2-carboxylic acid ((R)-2-amino-3-methyl-butyl)-amide,
3,5-Diamino-6-chloro-pyrazine-2-carboxylic acid {(S)-2-amino-6-[3-(4-benzyloxy-phenyl)-propionylamino]-hexyl}-amide,
3,5-Diamino-6-chloro-pyrazine-2-carboxylic acid ((R)-2-guanidino-butyl)-amide,
3,5-Diamino-6-chloro-pyrazine-2-carboxylic acid ((S)-2-guanidino-pentyl)-amide,
3,5-Diamino-6-chloro-pyrazine-2-carboxylic acid ((R)-2-guanidino-pentyl)-amide,
3,5-Diamino-6-chloro-pyrazine-2-carboxylic acid ((S)-3-cyclohexyl-2-guanidino-propyl)-amide,
3,5-Diamino-6-chloro-pyrazine-2-carboxylic acid {(S)-2-[3-(4-methoxy-phenyl)-propylamino]-pentyl}-amide,
3,5-Diamino-6-chloro-pyrazine-2-carboxylic acid {(S)-6-[2-(4-benzyloxy-phenyl)-acetylamino]-2-guanidino-hexyl}-amide,
3,5-Diamino-6-chloro-pyrazine-2-carboxylic acid ((S)-2-{N-[3-(4-methoxy-phenyl)-propyl]-guanidino}-pentyl)-amide,
3,5-Diamino-6-chloro-pyrazine-2-carboxylic acid ((R)-2-{N-[3-(4-methoxy-phenyl)-propyl]guanidino}-pentyl)-amide,
3,5-Diamino-6-chloro-pyrazine-2-carboxylic acid [(S)-2-(N-{3-[4-((S)-2,3-dihydroxy-propoxy)-phenyl]-propyl}-guanidino)-pentyl]-amide,
3,5-Diamino-6-chloro-pyrazine-2-carboxylic acid ((S)-2-{N'-[3-(4-methoxy-phenyl)-propyl]guanidino}-pentyl)-amide,
3,5-Diamino-6-chloro-pyrazine-2-carboxylic acid {(S)-2-[N'-(4-methoxy-benzyl)-guanidino]-pentyl}-amide,
3,5-Diamino-6-chloro-pyrazine-2-carboxylic acid {(R)-2-[N'-(4-methoxy-benzyl)-guanidino]-pentyl}-amide, and pharmaceutically acceptable salts thereof.

Definitions

Terms used in the specification have the following meanings:

"Optionally substituted" means the group referred to can be substituted at one or more positions by any one or any combination of the radicals listed thereafter.

"optionally substituted by one or more Z groups" denotes that the relevant group may include one or more substituents, each independently selected from the groups included within the definition of Z. Thus, where there are two or more Z group substituents, these may be the same or different.

"Halo" or "halogen", as used herein, may be fluorine, chlorine, bromine or iodine.

"$C_1$-$C_6$-Alkyl", as used herein, denotes straight chain or branched alkyl having 1-6 carbon atoms. If a different number of carbon atoms is specified, such as $C_4$ or $C_3$, then the definition is to be amended accordingly.

"$C_1$-$C_6$-Alkoxy", as used herein, denotes straight chain or branched alkoxy having 1-6 carbon atoms. If a different number of carbon atoms is specified, such as $C_4$ or $C_3$, then the definition is to be amended accordingly.

The term "alkylene" denotes a straight chain or branched saturated hydrocarbon chain containing the relevant number of carbon atoms.

The terms "—($C_1$-$C_4$ alkylene)-" or "—($C_1$-$C_3$ alkylene)-" denote a hydrocarbon linking group having the relevant number of carbon atoms "$C_3$-$C_{10}$-Carbocyclic group" or "$C_3$-$C_{10}$ cycloalkyl", as used herein, denotes a carbocyclic group having 3- to 10-ring carbon atoms that is saturated. Optionally, the ring system contains 3-6 carbon atoms, i.e. $C_3$-$C_6$ cycloalkyl or $C_3$-$C_6$ carbocyclic group. Examples of $C_3$-$C_{10}$-carbocyclic groups include but are not limited to cyclopropyl, cyclobutyl, cyclopentyl, cyclohexyl, cycloheptyl or cyclooctyl or a bicyclic group, such as bicyclooctyl, bicyclononyl including indanyl and bicyclodecyl. If a different number of carbon atoms is specified, such as $C_6$, then the definition is to be amended accordingly.

"$C_5$-$C_{10}$ cycloalkenyl", as used herein, denotes a non-aromatic carbocyclic group having 5- to 10-ring carbon atoms that contains one or more carbon-carbon double bonds. Optionally, the ring system contains 5 or 6 carbon atoms, i.e. $C_5$-$C_6$ cycloalkenyl.

The terms "aryl" and "$C_6$-$C_{15}$-Aromatic carbocyclic group", as used herein, denote an aromatic group having 6- to 15-ring carbon atoms. Examples of $C_6$-$C_{15}$-aromatic carbocyclic groups include, but are not limited to, phenyl, phenylene, benzenetriyl, naphthyl, naphthylene, naphthalenetriyl or anthrylene. If a different number of carbon atoms is specified, such as $C_{10}$ (e.g. a $C_6$-$C_{10}$ aryl group), then the definition is to be amended accordingly. In certain embodiments, aryl is phenyl or naphthylenyl. In further embodiments, aryl is phenyl.

The terms "heterocyclic group" and "4- to 10-Membered heterocyclic group" refer to 4- to 10-membered heterocyclic rings containing at least one ring heteroatom selected from the group consisting of nitrogen, oxygen and sulphur, which may be saturated or partially saturated. Examples of such heterocyclic groups include, but are not limited to, pyrrolidine, piperidine, piperazine, pyrrolidinone, morpholine, tetrahydrofuran, tetrahydrothiophene, tetrahydrothiopyran, tetrahydropyran, 1,4-dioxane and 1,4-oxathiane. Suitably, the heterocyclic group may be a 5- to 6-membered group.

The terms "heteroaryl group" and "heteroaromatic group" denote a 5- to 10-membered aromatic heterocyclic ring containing at least one ring heteroatom selected from the group consisting of nitrogen, oxygen and sulphur. Examples of such heteroaryl groups include, but are not limited to, pyrrole, pyrazole, imidazole, triazole, tetrazole, pyridine, pyridazine, pyrimidine, pyrazine, triazine, quinoline, isoquinoline, indole, isoindole, indolizine, indazole, benzimidazole, purine, quinolizine, cinnoline, quinazoline, quinoxaline, naphthyridine, phthalazine, pteridine, acridine, phenazine and phenanthroline. Suitably, the heteroaryl group may be a 5- to 6-membered group.

It is to be understood that any and all embodiments of the present invention may be taken in conjunction with any other embodiment to describe additional embodiments of the present invention. Furthermore, any elements of an embodiment are intended to be combinable with any and all other elements from any of the embodiments to describe additional embodiments. It is understood by those skilled in the art that combinations of substituents where not possible are not an aspect of the present invention.

A second aspect of the present invention provides for the use of a compound of formula (I) in any of the aforementioned embodiments, in free or pharmaceutically acceptable salt form, for the manufacture of a medicament for the treatment of an inflammatory or allergic condition, particularly an inflammatory or obstructive airways disease or mucosal hydration.

An embodiment of the present invention provides for the use of a compound of formula (I) in any of the aforementioned embodiments, in free or pharmaceutically acceptable salt form, for the manufacture of a medicament for the treatment of an inflammatory or allergic condition selected from cystic fibrosis, primary ciliary dyskinesia, chronic bronchitis, chronic obstructive pulmonary disease, asthma, respiratory tract infections, lung carcinoma, xerostomia and keratoconjunctivitis sire.

Throughout this specification and in the claims that follow, unless the context requires otherwise, the word "comprise", or variations, such as "comprises" or "comprising", will be understood to imply the inclusion of a stated integer or step or group of integers or steps but not the exclusion of any other integer or step or group of integers or steps.

Especially preferred specific compounds of formula (I) are those described hereinafter in the Examples.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid, hydroiodic acid, nitric acid, sulfuric acid, phosphoric acid; and organic acids, for example aliphatic monocarboxylic acids such as formic acid, acetic acid, trifluoroacetic acid, propionic acid and butyric acid, caprylic acid, dichloroacetic acid, hippuric acid, aliphatic hydroxy acids such as lactic acid, citric acid, tartaric acid or malic acid, gluconic acid, mandelic acid, dicarboxylic acids such as maleic acid or succinic acid, adipic acid, aspartic acid, fumaric acid, glutamic acid, malonic acid, sebacic acid, aromatic carboxylic acids such as benzoic acid, p-chloro-benzoic acid, nicotinic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid or p-toluenesulfonic acid. These salts may be prepared from compounds of formula I by known salt-forming procedures. Pharmaceutically acceptable solvates are generally hydrates.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine, arginine, benethamine, benzathine, diethanolamine, 4-(2-hydroxy-ethyl)morpholine, 1-(2-hydroxyethyl) pyrrolidine, N-methyl glutamine, piperazine, triethanolamine or tromethamine. These salts may be prepared from compounds of formula I by known salt-forming procedures. Compounds of formula I that contain acidic, e.g. carboxyl, groups may also exist as zwitterions with the quaternary ammonium centre.

Pharmaceutically acceptable solvates in accordance with the invention include those wherein the solvent of crystallisation may be isotopically substituted e.g. $D_2O$, $d_6$-acetone or $d_6$-DMSO.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2$H and $^3$H, carbon e.g. $^{11}$C, $^{13}$C and $^{14}$C, chlorine e.g. $^{36}$Cl, fluorine e.g. $^{18}$F, iodine e.g. $^{123}$I and $^{125}$I, nitrogen e.g. $^{13}$N and $^{15}$N, oxygen e.g. $^{15}$O, $^{17}$O and $^{18}$O, and sulfur e.g. $^{35}$S.

Certain isotopically-labelled compounds of formula I, for example those incorporating a radioactive isotope, are useful in drug and/or substrate tissue distribution studies. The radioactive isotopes tritium ($^3$H) and carbon-14 ($^{14}$C) are particularly useful for this purpose in view of their ease of incorporation and ready means of detection. Substitution with heavier isotopes such as deuterium ($^2$H) may afford certain therapeutic advantages that result from greater metabolic stability, for example increased in vivo half-life or reduced dosage requirements, and hence may be preferred in some circumstances. Substitution with positron emitting isotopes, such as $^{11}$C, $^{18}$F, $^{15}$O, and $^{13}$N can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using an appropriate isotopically-labelled reagent in place of the non-labelled reagent previously used.

Some of the compounds of Formula I may exist in different tautomeric forms. Tautomerism is well known to those skilled in the art and the skilled person will readily appreciate which groups are able to tautomerise to form the different tautomeric forms. The invention includes all tautomeric forms of the compounds of Formula I.

Synthesis

Generally, compounds according to Formula I can be synthesized by the routes described in Scheme 1 and the Examples.

For instance, intermediate 1 can be reacted with intermediate 2 in the presence of a suitable coupling agent and organic base in organic solvent to provide a compound of Formula I as the free base. The free base can then be converted to a salt form by treatment with an appropriate acid.

Intermediates can be prepared from methods known by those skilled in the art or are commercially available.

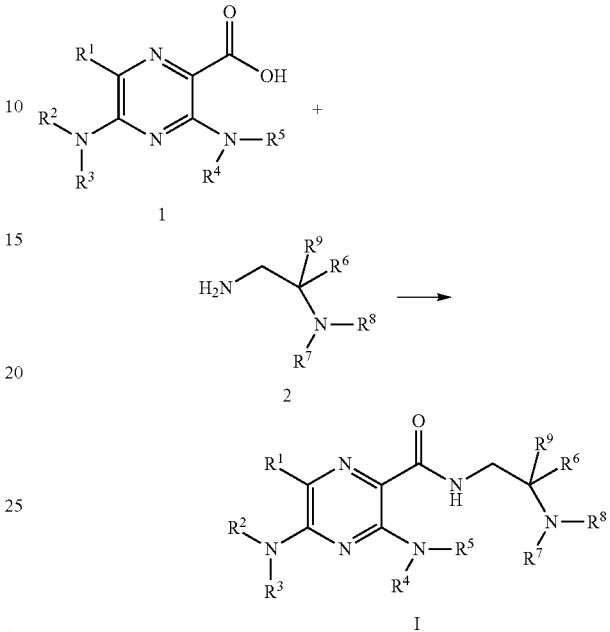

Scheme 1

Compounds of formula (I), in free form, may be converted into salt form, and vice versa, in a conventional manners understood by those skilled in the art. The compounds in free or salt form can be obtained in the form of hydrates or solvates containing a solvent used for crystallisation. Compounds of formula (I) can be recovered from reaction mixtures and purified in a conventional manner. Isomers, such as stereoisomers, may be obtained in a conventional manner, e.g., by fractional crystallisation or asymmetric synthesis from correspondingly asymmetrically substituted, e.g., optically active, starting materials.

The compounds of formula (I) can be prepared, e.g., using the reactions and techniques described below and in the Examples. The reactions may be performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention.

The various substituents on the synthetic intermediates and final products shown in the following reaction schemes can be present in their fully elaborated forms, with suitable protecting groups where required as understood by one skilled in the art, or in precursor forms which can later be elaborated into their final forms by methods familiar to one skilled in the art. The substituents can also be added at various stages throughout the synthetic sequence or after completion of the synthetic sequence. In many cases, commonly used functional group manipulations can be used to transform one intermediate into another intermediate, or one compound of formula (I) into another compound of formula (I). Examples of such manipulations are conversion of an ester or a ketone to an alcohol; conversion of an ester to a ketone; interconversions of esters, acids and amides; alkylation, acylation and sulfonylation of alcohols and amines; and many others. Substituents can also be added using common reactions, such as alkylation, acylation, halogenation or oxidation. Such manipulations are well-known in the art, and many reference works summarize procedures and methods for such manipulations. Some reference works which gives examples and references to the primary literature of organic synthesis for many functional group manipulations, as well as other transformations commonly used in the art of organic synthesis are *March's Organic Chemistry, 5th Edition*, Wiley and Chichester, Eds. (2001); *Comprehensive Organic Transformations*, Larock, Ed., VCH (1989); *Comprehensive Organic Functional Group Transformations*, Katritzky et al. (series editors), Pergamon (1995); and *Comprehensive Organic Synthesis*, Trost and Fleming (series editors), Pergamon (1991). It will also be recognized that another major consideration in the planning of any synthetic route in this field is the judicious choice of the protecting group used for protection of the reactive functional groups present in the compounds described in this invention. Multiple protecting groups within the same molecule can be chosen such that each of these protecting groups can either be removed without removal of other protecting groups in the same molecule, or several protecting groups can be removed using the same reaction step, depending upon the outcome desired. An authoritative account describing many alternatives to the trained practitioner is Greene and Wuts, *Protective Groups in Organic Synthesis*, Wiley and Sons (1999).

Pharmacological Activity

Having regard to their blockade of the epithelial sodium channel (ENaC), compounds of formula (I), in free or pharmaceutically acceptable salt form, hereinafter alternately referred to as "agents of the invention", are useful in the treatment of conditions which respond to the blockade of the epithelial sodium channel, particularly conditions benefiting from mucosal hydration.

Diseases treatable by blockade of the epithelial sodium channel, include diseases associated with the regulation of fluid volumes across epithelial membranes. For example, the volume of airway surface liquid is a key regulator of mucociliary clearance and the maintenance of lung health. The blockade of the epithelial sodium channel will promote fluid accumulation on the mucosal side of the airway epithelium thereby promoting mucus clearance and preventing the accumulation of mucus and sputum in respiratory tissues (including lung airways). Such diseases include respiratory diseases, such as cystic fibrosis, primary ciliary dyskinesia, chronic bronchitis, chronic obstructive pulmonary disease (COPD), asthma, respiratory tract infections (acute and chronic; viral and bacterial) and lung carcinoma. Diseases treatable by blockade of the epithelial sodium channel also include diseases other than respiratory diseases that are associated with abnormal fluid regulation across an epithelium, perhaps involving abnormal physiology of the protective surface liquids on their surface, e.g., xerostomia (dry mouth) or keratoconjunctivitis sire (dry eye). Furthermore, blockade of the epithelial sodium channel in the kidney could be used to promote diuresis and thereby induce a hypotensive effect.

Treatment in accordance with the invention may be symptomatic or prophylactic.

Asthma includes both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g., of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".)

Prophylactic efficacy in the treatment of asthma will be evidenced by reduced frequency or severity of symptomatic attack, e.g., of acute asthmatic or bronchoconstrictor attack, improvement in lung function or improved airways hyperreactivity. It may further be evidenced by reduced requirement for other, symptomatic therapy, i.e., therapy for or intended to restrict or abort symptomatic attack when it occurs, e.g., anti-inflammatory (e.g., cortico-steroid) or bronchodilatory. Prophylactic benefit in asthma may, in particular, be apparent in subjects prone to "morning dipping". "Morning dipping" is a recognized asthmatic syndrome, common to a substantial percentage of asthmatics and characterized by asthma attack, e.g., between the hours of about 4-6 am, i.e., at a time normally substantially distant from any previously administered symptomatic asthma therapy.

Chronic obstructive pulmonary disease includes chronic bronchitis or dyspnea associated therewith, emphysema, as well as exacerbation of airways hyperreactivity consequent to other drug therapy, in particular, other inhaled drug therapy. The invention is also applicable to the treatment of bronchitis of whatever type or genesis including, e.g., acute, arachidic, catarrhal, croupus, chronic or phthinoid bronchitis.

The suitability of epithelial sodium channel blocker as a treatment of a disease benefiting from mucosal hydration, may be tested by determining the inhibitory effect of the epithelial sodium channel blocker on: the ion channel/ion transport function in suitable isolated cells or confluent epithelia using the methods described in Hirsh et al., *J Pharm Exp Ther* (2004).

Epithelial sodium channel blockers, including the compounds of formula (I), are also useful as co-therapeutic agents for use in combination with other drug substances, such as anti-inflammatory, bronchodilatory, antihistamine or anti-tussive drug substances, particularly in the treatment of cystic fibrosis or obstructive or inflammatory airways diseases such as those mentioned hereinbefore, e.g., as potentiators of therapeutic activity of such drugs or as a means of reducing required dosing or potential side effects of such drugs.

The epithelial sodium channel blocker may be mixed with the other drug substance in a fixed pharmaceutical composition or it may be administered separately, before, simultaneously with or after the other drug substance.

Accordingly, the invention includes as a further aspect a combination of epithelial sodium channel blocker with osmotic agents (hypertonic saline, dextran, mannitol, Xylitol)+modifiers of CFTR function, both wild-type and mutant (correctors+potentiators), e.g., those described in WO 2007/021982, WO 2006/099256, WO 2006/127588, WO 2004/080972, WO 2005/026137, WO 2005/035514, WO 2005/075435, WO 2004/111014, WO 2006/101740, WO 2004/110352, WO 2005/120497 and US 2005/0176761, an anti-inflammatory, bronchodilatory, antihistamine, anti-tussive, antibiotic or DNase drug substance, said epithelial sodium channel blocker and said drug substance being in the same or different pharmaceutical composition.

Suitable antibiotics include macrolide antibiotics, e.g., tobramycin (TOBI™).

Suitable DNase drug substances include dornase alfa (Pulmozyme™), a highly-purified solution of recombinant human deoxyribonuclease I (rhDNase), which selectively cleaves DNA. Dornase alfa is used to treat cystic fibrosis.

Other useful combinations of epithelial sodium channel blockers with anti-inflammatory drugs are those with antagonists of chemokine receptors, e.g., CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists, such as Schering-Plough antagonists SC-351125, SCH-55700 and SCH-D; Takeda antagonists, such as N-[[4-[[[6,7-dihydro-2-(4-methyl-phenyl)-5H-benzo-cyclohepten-8-yl]carbonyl]amino]phenyl]-methyl] tetrahydro-N,N-dimethyl-2H-pyran-4-amin-ium chloride (TAK-770); and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Suitable anti-inflammatory drugs include steroids, in particular, glucocorticosteroids, such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935 and WO 04/26248; LTD4 antagonists, such as montelukast and zafirlukast; PDE4 inhibitors, such as cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; adenosine A2B receptor antagonists such as those described in WO 02/42298; and beta-2 adrenoceptor agonists, such as albuterol (salbutamol), metaproterenol, terbutaline, salmeterol fenoterol, procaterol, and especially, formoterol, carmoterol and pharmaceutically acceptable salts thereof, and compounds (in free or salt or solvate form) of formula (I) of WO 0075114, which document is incorporated herein by reference, preferably compounds of the Examples thereof, especially a compound of formula:

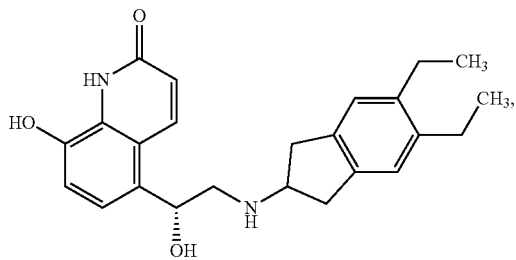 [SMILES: CCc1cc2c(cc1CC)CC(NC[C@H](O)c1ccc(O)c3[nH]c(=O)ccc13)C2]

corresponding to indacaterol and pharmaceutically acceptable salts thereof, as well as compounds (in free or salt or solvate form) of formula (I) of WO 04/16601, and also compounds of EP 1440966, JP 05025045, WO 93/18007, WO 99/64035, USP 2002/0055651, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618, WO 04/46083, WO 04/80964, WO 04/108765 and WO 04/108676.

Suitable bronchodilatory drugs include anticholinergic or antimuscarinic agents, in particular, ipratropium bromide, oxitropium bromide, tiotropium salts and CHF 4226 (Chiesi), and glycopyrrolate, but also those described in EP 424021, U.S. Pat. No. 3,714,357, U.S. Pat. No. 5,171,744, WO 01/04118, WO 02/00652, WO 02/51841, WO 02/53564, WO 03/00840, WO 03/33495, WO 03/53966, WO 03/87094, WO 04/018422 and WO 04/05285.

Suitable dual anti-inflammatory and bronchodilatory drugs include dual beta-2 adrenoceptor agonist/muscarinic antagonists such as those disclosed in USP 2004/0167167, WO 04/74246 and WO 04/74812.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine, as well as those disclosed in JP 2004107299, WO 03/099807 and WO 04/026841.

In accordance with the foregoing, the invention also provides as a further aspect a method for the treatment of a condition responsive to blockade of the epithelial sodium channel, e.g., diseases associated with the regulation of fluid volumes across epithelial membranes, particularly an obstructive airways disease, which comprises administering to a subject, particularly a human subject, in need thereof a compound of formula (I), in free form or in the form of a pharmaceutically acceptable salt.

In another aspect the invention provides a compound of formula (I), in free form or in the form of a pharmaceutically acceptable salt, for use in the manufacture of a medicament for the treatment of a condition responsive to blockade of the epithelial sodium channel, particularly an obstructive airways disease, e.g., cystic fibrosis and COPD.

The agents of the invention may be administered by any appropriate route, e.g. orally, e.g., in the form of a tablet or capsule; parenterally, e.g., intravenously; by inhalation, e.g., in the treatment of an obstructive airways disease; intranasally, e.g., in the treatment of allergic rhinitis; topically to the skin; or rectally. In a further aspect, the invention also provides a pharmaceutical composition comprising a compound of formula (I), in free form or in the form of a pharmaceutically acceptable salt, optionally together with a pharmaceutically acceptable diluent or carrier therefor. The composition may contain a co-therapeutic agent, such as an anti-inflammatory, broncho-dilatory, antihistamine or anti-tussive drug as hereinbefore described. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g., patches. Compositions for inhalation may comprise aerosol or other atomizable formulations or dry powder formulations. When the composition comprises an aerosol formulation, it preferably contains, e.g., a hydro-fluoro-alkane (HFA) propellant, such as HFA134a or HFA227 or a mixture of these, and may contain one or more co-solvents known in the art, such as ethanol (up to 20% by weight), and/or one or more surfactants, such as oleic acid or sorbitan trioleate, and/or one or more bulking agents, such as lactose. When the composition comprises a dry powder formulation, it preferably contains, e.g., the compound of formula (I) having a particle diameter up to 10 microns, optionally together with a diluent or carrier, such as lactose, of the desired particle size distribution and a compound that helps to protect against product performance deterioration due to moisture, e.g., magnesium stearate. When the composition comprises a nebulised formulation, it preferably contains, e.g., the compound of formula (I) either dissolved, or suspended, in a vehicle containing water, a co-solvent, such as ethanol or propylene glycol and a stabilizer, which may be a surfactant.

Further aspects of the invention include:
(a) a compound of formula (I) in inhalable form, e.g., in an aerosol or other atomisable composition or in inhalable particulate, e.g., micronised form;
(b) an inhalable medicament comprising a compound of formula (I) in inhalable form;
(c) a pharmaceutical product comprising a compound of formula (I) in inhalable form in association with an inhalation device; and
(d) an inhalation device containing a compound of formula I in inhalable form.

Dosages of compounds of formula (I) employed in practising the present invention will of course vary depending, e.g., on the particular condition to be treated, the effect desired and the mode of administration. In general, suitable daily dosages for administration by inhalation are of the order of 0.005-10 mg, while for oral administration suitable daily doses are of the order of 0.05-100 mg.

Pharmaceutical Use and Assay

Compounds of formula (I) and their pharmaceutically acceptable salts, hereinafter referred to alternatively as "agents of the invention", are useful as pharmaceuticals. In particular, the compounds have good ENaC blocker activity and may be tested in the following assays.

Cell Culture

Human Bronchial Epithelial cells (HBECs) (Cambrex) were cultured under air-liquid interface conditions to provide a well differentiated mucociliary phenotype.

HBECs were cultured using a modification of the method described by Gray and colleagues (Gray et al., 1996). Cells were seeded in plastic T-162 flasks and were grown in bronchial epithelial cell growth medium (BEGM; Cambrex) supplemented with bovine pituitary extract (52 μg/mL), hydrocortisone (0.5 μg/mL), human recombinant epidermal growth factor (0.5 ng/mL), epinephrine (0.5 μg/mL), transferrin (10 μg/mL), insulin (5 μg/mL), retinoic acid (0.1 μg/mL), triiodothyronine (6.5 μg/mL), gentamycin (50 μg/mL) and amphotericin B (50 ng/mL). Medium was changed every 48 hours until cells were 90% confluent. Cells were then passaged and seeded ($8.25 \times 10^5$ cells/insert) on polycarbonate Snapwell inserts (Costar) in differentiation media containing 50% DMEM in BEGM with the same supplements as above but without triiodothyronine and a final retinoic acid concentration of 50 nM (all-trans retinoic acid). Cells were maintained submerged for the first 7 days in culture, after which time they were exposed to an apical air interface for the remainder of the culture period. At this time, media was changed to DMEM:F12 media containing 2% v/v Ultroser G for the remainder of culture. Amphotericin B was removed from all media 3 feeds prior to use in the Ussing Chambers. Cells were used between days 7 and 21 after establishment of the apical-air interface. At all stages of culture, cells were maintained at 37° C. in 5% $CO_2$ in an air incubator.

Short Circuit Current (ISC) Measurements

Snapwell inserts were mounted in Vertical Diffusion Chambers (Costar) and were bathed with continuously gassed Ringer solution (5% $CO_2$ in $O_2$; pH 7.4) maintained at 37° C. containing (in mM): 120 NaCl, 25 $NaHCO_3$, 3.3 $KH_2PO_4$, 0.8 $K_2HPO_4$, 1.2 $CaCl_2$, 1.2 $MgCl_2$, and 10 glucose. The solution osmolarity was between 280 and 300 mOsmol/kg $H_2O$ for all physiological salt solutions used. Cells were voltage clamped to 0 mV (model EVC4000; WPI). RT was measured by applying a 1- or 2-mV pulse at 30-s intervals and calculating RT by Ohm's law. Data were recorded using a PowerLab workstation (ADInstruments).

Test compounds were prepared as a 10 mM stock solution in DMSO (95%). Serial 3-fold dilutions were freshly prepared in an appropriate vehicle (distilled $H_2O$ or Ringers solution). The initial concentration was added to the apical chamber as a 1000× concentrate in 5 μL, resulting in a final 1× concentration the 5 mL volume of the Ussing chamber. Subsequent additions of compound were added in a 3.3 μL volume of the 1000× serially diluted stock solution. At the completion of the concentration-response experiment, amiloride (10 μM) was added into the apical chamber to enable the total amiloride-sensitive current to be measured. An amiloride control $IC_{50}$ was established at the start of each experiment.

Results are expressed as the mean % inhibition of the amiloride-sensitive ISC. Concentration-response curves were plotted and $IC_{50}$ values generated using GraphPad Prism 3.02. Cell inserts were typically run in duplicate and the $IC_{50}$ calculated on the mean % inhibition data.

Compounds of the Examples, herein below, generally have $IC_{50}$ values in the data measurements described above below 10 μM. For example, the compounds of Examples 4, 9, 11, 12, 21, 24, 26, 27, 29, 31 and 32 have $IC_{50}$ values of 0.29, 2.74, 5.90, 0.032, 0.064, 0.045, 0.060, 0.20, 0.005, 0.049 and 0.006 μM, respectively.

The invention is illustrated by the following Examples.

EXAMPLES

Example compounds of the present invention include compounds of formula Ia which are shown in Table 1 below. The method of preparation being described hereinafter.

TABLE 1

| Ex. | Structure | [M + H]⁺ |
|---|---|---|
| 1 | (structure) | 299 |

TABLE 1-continued

| Ex. | Structure | [M + H]⁺ |
|---|---|---|
| 2 | 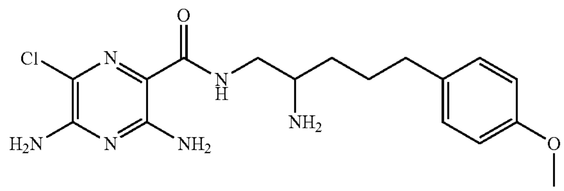 [SMILES: COc1ccc(CCCC(N)CNC(=O)c2nc(Cl)c(N)nc2N)cc1] | 379 |
| 3 | 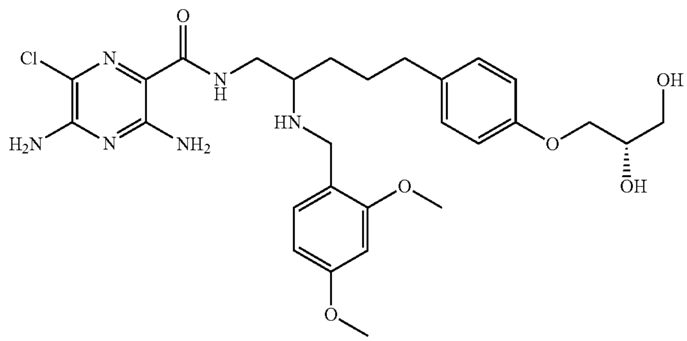 [SMILES: COc1ccc(CNC(CCCc2ccc(OC[C@@H](O)CO)cc2)CNC(=O)c2nc(Cl)c(N)nc2N)c(OC)c1] | 589 |
| 4 | 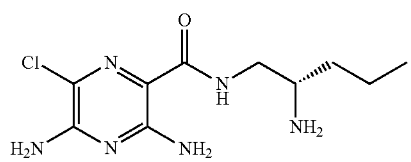 [SMILES: CCC[C@H](N)CNC(=O)c1nc(Cl)c(N)nc1N] | 273 |
| 5 | 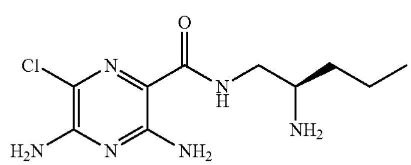 [SMILES: CCC[C@@H](N)CNC(=O)c1nc(Cl)c(N)nc1N] | 273 |
| 6 | 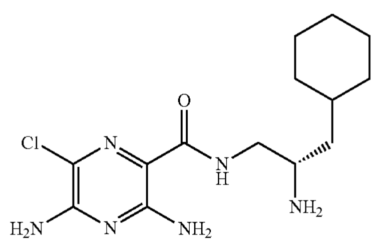 [SMILES: Nc1nc(N)c(C(=O)NC[C@@H](N)CC2CCCCC2)nc1Cl] | 327 |
| 7 | 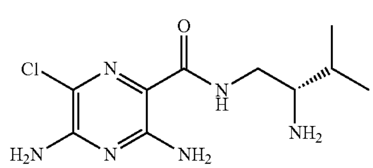 [SMILES: CC(C)[C@H](N)CNC(=O)c1nc(Cl)c(N)nc1N] | 273 |
| 8 | 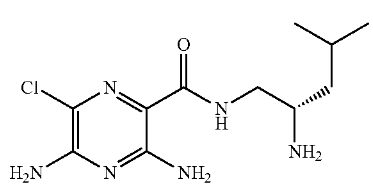 [SMILES: CC(C)C[C@H](N)CNC(=O)c1nc(Cl)c(N)nc1N] | 287 |

TABLE 1-continued

| Ex. | Structure | [M + H]+ |
|---|---|---|
| 9 | (structure) | 271 |
| 10 | (structure) | 285 |
| 11 | (structure) | 285 |
| 12 | (structure) Chiral | 526 |
| 13 | (structure) Chiral | 287 |
| 14 | (structure) Chiral | 259 |
| 15 | (structure) | 245 |

TABLE 1-continued

| Ex. | Structure | [M + H]⁺ |
|---|---|---|
| 16 | Chiral | 259 |
| 17 | Chiral | 245 |
| 18 | Chiral | 285 |
| 19 | Chiral | 271 |
| 20 | Chiral | 273 |
| 21 | 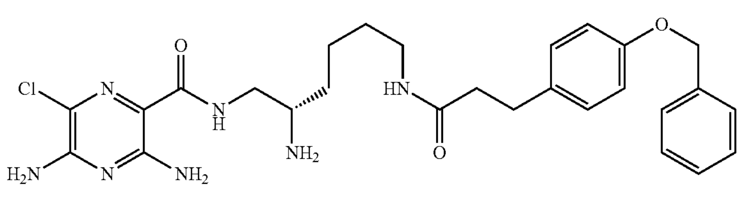 [SMILES: Nc1nc(N)c(C(=O)NC[C@@H](N)CCCCNC(=O)CCc2ccc(OCc3ccccc3)cc2)nc1Cl] | 540 |
| 22 | Chiral | 301 |

TABLE 1-continued
| Ex. | Structure | [M + H]+ |
|---|---|---|
| 23 | 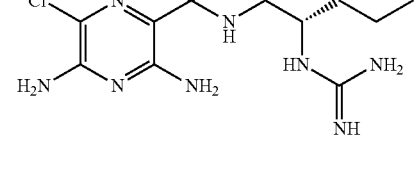 Chiral | 315 |
| 24 | 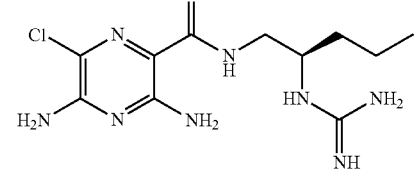 Chiral | 315 |
| 25 | 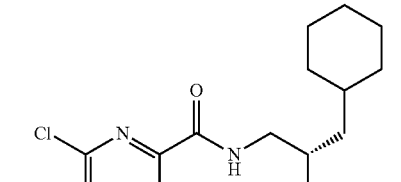 Chiral | 369 |
| 26 | 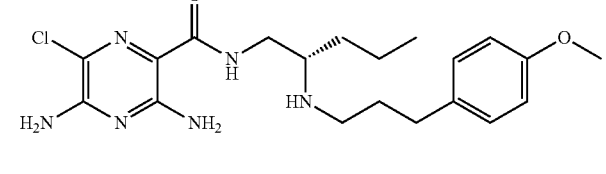 | 421 |
| 27 | 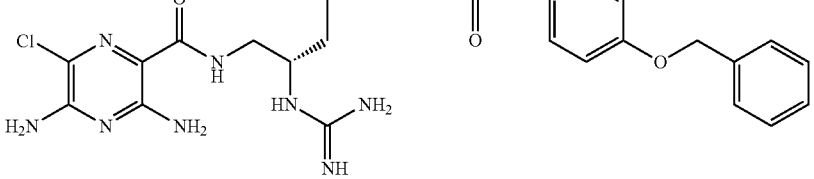 Chiral | 568 |
| 28 | 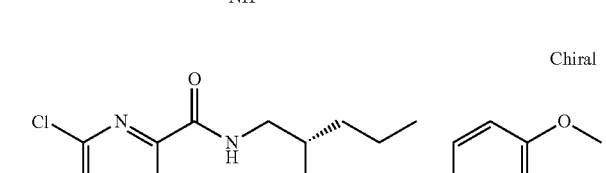 Chiral | 463 |

TABLE 1-continued

| Ex. | Structure | [M + H]+ |
|---|---|---|
| 29 | Chiral | 463 |
| 30 | Chiral | 523 |
| 31 | 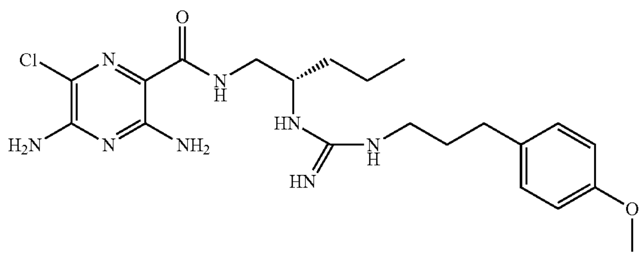 [SMILES: CCC[C@@H](CNC(=O)c1nc(Cl)c(N)nc1N)NC(=N)NCCCc1ccc(OC)cc1] | 463.2 |
| 32 | Chiral | 435.2 |
| 33 | Chiral | 435.3 |

Referring to the examples that follow, compounds of the preferred embodiments are synthesized using the methods described herein, or other methods, which are known in the art.

It should be understood that the organic compounds according to the preferred embodiments may exhibit the phenomenon of tautomerism. As the chemical structures within this specification can only represent one of the possible tautomeric forms, it should be understood that the preferred embodiments encompasses any tautomeric form of the drawn structure.

It is understood that the invention is not limited to the embodiments set forth herein for illustration, but embraces all such forms thereof as come within the scope of the above disclosure.

General Conditions:

Mass spectra are run on LCMS systems using electrospray ionization. These are either Agilent 1100 HPLC/Micromass Platform Mass Spectrometer combinations or Waters Acquity HPLC with SQD Mass Spectrometer. [M+H]+ refers to mono-isotopic molecular weights.

The various starting materials, intermediates, and compounds of the preferred embodiments may be isolated and purified, where appropriate, using conventional techniques such as precipitation, filtration, crystallization, evaporation, distillation, and chromatography. Unless otherwise stated, all starting materials are obtained from commercial suppliers and used without further purification. Salts may be prepared from compounds by known salt-forming procedures.

In addition various trade reagents and materials available from have been utilized. Such reagents and materials include: Isolute™ (available from Biotage) and Celite® (available from Aldrich) and can be readily obtained from the suppliers indicated.

For the examples below as well as throughout the application, the following abbreviations have the following meanings. If not defined, the terms have their generally accepted meanings.

| Abbreviations: | |
|---|---|
| RT | room temperature |
| DMF | dimethyl-formamide |
| THF | tetrahydrofuran |
| MeOH | methanol |
| DCM | dichloromethane |
| EtOAc | ethyl acetate |
| EtOH | ethanol |
| LCMS | liquid chromatographic mass spectroscopy |
| TEA | triethylamine |
| TFA | trifluoroacetic acid |
| HPLC | high performance liquid chromatography |
| DMSO | dimethyl sulfoxide |
| Et$_3$N | triethylamine |
| HPLC | high performance liquid chromatography |
| HATU | O-(7-azabenzotriazole-1-yl)-N,N,N',N'-tetramethyluronium hexafluorophosphate |
| CDI | 1,1'-carbonyl-diimidazole |
| DEAD | diethylazodicarboxylate |
| PS | polymer-supported |
| 9-BBN | 9-borabiclyclo[3.3.1]nonane |
| dppf | (diphenylphosphino)ferrocene |

Preparation of Final Compounds

Example 1

3,5-Diamino-6-chloro-pyrazine-2-carboxylic acid ((R)-1-ethyl-pyrrolidin-2-ylmethyl)-amide trifluoroacetate To a solution of 3,5-diamino-6-chloro-pyrazine-2-carboxylic acid (0.20 g, 1.06 mmol) and HATU (0.404 g, 1.06 mmol) in DMF (5 mL) is added N-methylmorpholine (0.466 mL, 4.25 mmol) followed by (R)-(+)-2-aminomethyl-1-ethylpyrrolidine (0.136 g, 1.06 mmol) and the reaction mixture is stirred at RT overnight. The solvent is removed in vacuo and the crude product is purified by reverse phase column chromatography (Isolute™ C18, 0-100% acetonitrile in water with 0.1% TFA) to afford the title compound. [M+H]$^+$ 299. $^1$H NMR (400 MHz, MeOD-d4) δ 3.81 (1H, dd), 3.75-3.66 (2H, m), 3.62-3.54 (2H, m), 3.21-3.12 (2H, m), 2.29-1.94 (4H, m), 1.41 (3H, t).

Example 2

3,5-Diamino-6-chloro-pyrazine-2-carboxylic acid [2-amino-5-(4-methoxy-phenyl)-pentyl]-amide trifluoroacetate To a solution of 3,5-diamino-6-chloro-pyrazine-2-carboxylic acid (0.21 g, 1.09 mmol) and HATU (0.42 g, 1.09 mmol) in DMF (10 mL) is added N-methylmorpholine (0.48 mL, 4.40 mmol) followed by 2-(tert-butoxymethyl-amino)-5-(4-methoxy-phenyl)-pentanoic acid amide (Intermediate A) (0.35 g, 1.09 mmol) and the mixture is stirred at RT overnight. The reaction mixture is filtered and the filtrate is concentrated in vacuo. The residue is triturated with water (2×15 mL) and the resulting solid is taken up in MeOH (20 mL) and the suspension is heated to reflux for 0.5 h. After this time the solid impurities are removed by filtration. To the filtrate is added DCM (10 mL) and TFA (2 mL) and the reaction is stirred at RT for 1 h, after which time the reaction mixture is concentrated in vacuo. The resulting residue is purified by reverse phase column chromatography (Isolute™ C18, 0-100% acetonitrile in water with 0.1% TFA) to afford the title compound as a racemic mixture. [M+H]$^+$ 379. $^1$H NMR (400 MHz, MeOD-d$_4$) δ 7.12 (2H, d), 6.82 (2H, d), 3.75 (3H, s), 3.47-3.37 (2H, m), 3.39-3.31 (1H, m), 2.64 (2H, t), 1.81-1.52 (4H, m).

Example 3

3,5-Diamino-6-chloro-pyrazine-2-carboxylic acid [5-[4-((S)-2,3-dihydroxy-propoxy)-phenyl]-2-(2,4-dimethoxy-benzylamino)-pentyl]-amide Step 1: 2-(2,4-Dimethoxy-benzylamino)-5-[4-((R)-2,2-dimethyl-[1,3]dioxolan-4-ylmethoxy)-phenyl]-pentanenitrile To a solution of 2-amino-5-[4-((R)-2,2-dimethyl-[1,3]dioxolan-4-ylmethoxy)-phenyl]-pentanenitrile (Intermediate B) (480 mg, 1.6 mmol) in DCM (13 mL) is added 2,4-dimethoxybenzaldehyde (319 mg, 1.92 mmol) and sodium triacetoxyborohydride (529 mg, 2.49 mmol) and the reaction is stirred at RT for 15 h. After this time saturated aqueous sodium hydrogen carbonate solution (20 mL) is added and the reaction is stirred at RT for 0.5 h. DCM (20 mL) is added and the layers are separated. The organic phase is washed with brine (20 mL) then dried over Na$_2$SO$_4$ and the solvent is removed in vacuo. Chromatography (SiO$_2$, EtOAc:iso-hexane 2:3) affords the title compound as a colourless oil.

Step 2: N*2*-(2,4-Dimethoxy-benzyl)-5-[4-((R)-2,2-dimethyl-[1,3]dioxolan-4-ylmethoxy)-phenyl]-pentane-1,2-diamine To a solution of 2-(2,4-dimethoxy-benzylamino)-5-[4-((R)-2,2-dimethyl-[1,3]dioxolan-4-ylmethoxy)-phenyl]-pentanenitrile (513 mg, 1.12 mmol) in diethyl ether (15 mL) under argon is slowly added lithium aluminium hydride (2.25 mL of a 1.0 M solution in diethyl ether, 2.25 mmol). The resulting reaction mixture is stirred at RT for 3 h, then is left standing at RT overnight. Water (0.1 mL) is added cautiously, followed by sodium hydroxide (0.2 mL of a 15% aqueous solution) and a further portion of water (0.1 mL). The reaction mixture is diluted with diethyl ether (5 mL) and then dried over MgSO$_4$ and the solvent is concentrated in vacuo to afford the title compound as a pale yellow oil that is used without further purification. [M+H]$^+$ 459.

Step 3: 3,5-Diamino-6-chloro-pyrazine-2-carboxylic acid {2-(2,4-dimethoxy-benzylamino)-5-[4-((S)-2,2-dimethyl-[1,3]dioxolan-4-ylmethoxy)-phenyl]-pentyl}-amide To a solution of 3,5-diamino-6-chloro-pyrazine-2-carboxylic acid (161 mg, 0.86 mmol) and HATU (325 mg, 0.86 mmol) in DMF (10 mL) is added N-methylmorpholine (0.38 mL, 3.42 mmol) followed by N*2*-(2,4-dimethoxy-benzyl)-5-[4-((R)-2,2-dimethyl-[1,3]dioxolan-4-ylmethoxy)-phenyl]-pentane-1,2-diamine (391 mg, 0.86 mmol) and the mixture is stirred at RT overnight. The solvent is removed in vacuo. To the crude residue is added water (10 mL), which is then decanted off to leave an orange solid that is washed with diethyl ether (10 mL) and dried in vacuo at 50° C. to afford the title compound. [M+H]$^+$ 629.

Step 4: 3,5-Diamino-6-chloro-pyrazine-2-carboxylic acid [5-[4-((S)-2,3-dihydroxy-propoxy)-phenyl]-2-(2,4-dimethoxy-benzylamino)-pentyl]amide To a solution of 3,5-diamino-6-chloro-pyrazine-2-carboxylic acid {2-(2,4-dimethoxy-benzylamino)-5-[4-((R)-2,2-dimethyl-[1,3]dioxolan-4-ylmethoxy)-phenyl]-pentyl}-amide (391 mg, 0.62 mmol) in DCM (3 mL) is added TFA (3 mL) and the reaction is stirred at RT for 72 h. The solvent is removed in vacuo and the residue is diluted with water (20 mL) and EtOAc (20 mL). The layers are separated and the aqueous phase is neutralised with aqueous sodium hydroxide and then extracted with EtOAc (2×20 mL). The EtOAc extracts are combined and dried (MgSO$_4$), filtered and the solvent is removed in vacuo. Chromatography (SiO$_2$, MeOH:DCM, 1:9) affords the title compound as a colourless solid as a mixture of diastereoisomers. [M+H]$^+$ 589. $^1$H NMR (400 MHz, CDCl$_3$) δ 7.63 (1H, br), 7.05 and 7.04 (1H, 2×d), 6.98 and 6.97 (2H, 2×d), 6.73 and 6.71 (2H 2×d), 6.36 and 6.35 (1H, 2×d), 6.34 and 6.30 (1H, 2×s), 5.15 (2H, br), 4.08-3.59 (8H, m), 3.71 (3H, s), 3.65 (3H, s), 3.50-3.41 (2H, m) 2.55 and 2.49 (2H, 2×t), 1.80-1.29 (4H, m).

Example 4

3,5-Diamino-6-chloro-pyrazine-2-carboxylic acid ((S)-2-amino-pentyl)-amide hydrochloride Step 1: [(S)-1-(1,3-Dioxo-1,3-dihydro-isoindol-2-ylmethyl)-butyl]-carbamic acid tert-butyl ester To a mixture of phthalimide (1.43 g, 9.72 mmol), ((S)-1-hydroxymethyl-butyl)-carbamic acid tert-butyl ester (prepared according to the procedure described in US 2007/0032433 page 232) (1.97 g, 9.69 mmol) and triphenylphosphine (2.55 g, 9.72 mmol) in DCM (25 mL) at 0° C. is added DEAD (1.6 mL, 10.2 mmol) dropwise. The reaction mixture is stirred at RT overnight. The reaction mixture is adsorbed onto SiO$_2$ and purification by chromatography (SiO$_2$, EtOAc/iso-hexane, gradient of 0-15% EtOAc) affords the title compound as white solid. [M+H]$^+$ 233.

Step 2: ((S)-1-Aminomethyl-butyl)-carbamic acid tert-butyl ester

A mixture of [(S)-1-(1,3-dioxo-1,3-dihydro-isoindol-2-ylmethyl)-butyl]-carbamic acid tert-butyl ester (2.80 g, 8.42 mmol) and hydrazine monohydrate (3.0 mL, 60.0 mmol) in EtOH (50 mL) and DCM (75 mL) is stirred at RT for 48 h. The precipitated solid is collected by filtration and washed with DCM to afford the crude product as a white solid that is used without further purification.

Step 3: ((S)-1-{[(3,5-Diamino-6-chloro-pyrazine-2-carbonyl)-amino]-methyl}-butyl)-carbamic acid tert-butyl ester A mixture of ((S)-1-aminomethyl-butyl)-carbamic acid tert-butyl ester (1.70 g, 8.40 mmol), 3,5-diamino-6-chloro-pyrazine-2-carboxylic acid (1.59 g, 8.43 mmol), N-methylmorpholine (3.8 mL, 34.5 mmol) and HATU (3.2 g, 8.42 mmol) in anhydrous DMF (50 mL) is stirred at RT for 16 h. The reaction mixture is concentrated in vacuo and the resulting residue is purified by column chromatography (basic alumina, MeOH:DCM) to afford the title compound as yellow solid. [M+H]$^+$ 333.

Step 4: 3,5-Diamino-6-chloro-pyrazine-2-carboxylic acid ((S)-2-amino-pentyl)-amide hydrochloride To a solution of ((S)-1-{[(3,5-diamino-6-chloro-pyrazine-2-carbonyl)-amino]-methyl}-butyl)-carbamic acid tert-butyl ester (1.30 g, 3.49 mmol) in 1,4-dioxane (20 mL) is added HCl (50 mL of a 4 M solution in 1,4-dioxane, 200 mmol) and the reaction mixture is stirred at RT for 16 h. The reaction mixture is concentrated in vacuo and the yellow solid obtained is triturated with diethyl ether; the diethyl ether layer is decanted and the product is dissolved in a minimal volume of MeOH and is precipitated by the addition of diethyl ether. The solvent is decanted and the resulting solid is dried under vacuum to afford the title compound. [M+H]$^+$ 233. $^1$H NMR (400 MHz, CDCl$_3$) δ 8.16 (1H, t), 7.89 (2H, br), 7.07 (4H, br), 3.42-3.38 (2H, m), 3.27-3.18 (1H, m), 1.54-1.47 (2H, m), 1.44-1.35 (2H, m), 0.89 (3H, t).

Example 5

3,5-Diamino-6-chloro-pyrazine-2-carboxylic acid ((R)-2-amino-pentyl)-amide hydrochloride The title compound is prepared by an analogous procedure to Example 4 by replacing ((S)-1-hydroxymethyl-butyl)-carbamic acid tert-butyl ester in step 1 with ((R)-1-hydroxymethyl-butyl)-carbamic acid tert-butyl ester (prepared according to the procedure described in WO1998/050029 page 638). [M+H]$^+$ 233.

Example 6

3,5-Diamino-6-chloro-pyrazine-2-carboxylic acid ((S)-2-amino-3-cyclohexyl-propyl)-amide hydrochloride The title compound is prepared by an analogous procedure to Example 4 by replacing ((S)-1-aminomethyl-butyl)-carbamic acid tert-butyl ester in step 3 with ((S)-1-aminomethyl-2-cyclohexyl-ethyl)-carbamic acid tert-butyl ester (prepared according to the procedure described in WO 2007/070201 page 177). [M+H]$^+$ 327.

Example 7

3,5-Diamino-6-chloro-pyrazine-2-carboxylic acid ((S)-2-amino-3-methyl-butyl)-amide hydrochloride The title compound is prepared by an analogous procedure to Example 4 by replacing ((S)-1-hydroxymethyl-butyl)-carbamic acid tert-butyl ester in step 1 with N-(tert-butoxycarbonyl)-L-valinol. [M+H]$^+$ 273.

Example 8

3,5-Diamino-6-chloro-pyrazine-2-carboxylic acid ((S)-2-amino-4-methyl-pentyl)-amide hydrochloride The title compound is prepared by an analogous procedure to Example 4 by replacing ((S)-1-aminomethyl-butyl)-carbamic acid tert-butyl ester in step 3 with ((S)-1-aminomethyl-3-methyl-butyl)-carbamic acid tert-butyl ester. [M+H]$^+$ 287.

Example 9

3,5-Diamino-6-chloro-pyrazine-2-carboxylic acid ((S)-1-pyrrolidin-2-ylmethyl)-amide hydrochloride The title compound is prepared by an analogous procedure to Example 4 by replacing ((S)-1-aminomethyl-butyl)-carbamic acid tert-butyl ester in step 3 with (S)-2-aminomethyl-1-N-Boc-pyrrolidine. [M+H]$^+$ 271.

Example 10

3,5-Diamino-6-chloro-pyrazine-2-carboxylic acid ((R)-1-piperidin-2-ylmethyl)-amide hydrochloride The title compound is prepared by an analogous procedure to Example 4 by replacing ((S)-1-aminomethyl-butyl)-carbamic acid tert-butyl ester in step 3 with (R)-2-aminomethyl-1-N-Boc-piperidine. [M+H]$^+$ 285.

Example 11

3,5-Diamino-6-chloro-pyrazine-2-carboxylic acid (1-amino-cyclopentylmethyl)-amide hydrochloride The title compound is prepared by an analogous procedure to Example 4 by replacing ((S)-1-aminomethyl-butyl)-carbamic acid tert-butyl ester in Step 3 with (1-aminomethyl-cyclopentyl)-carbamic acid tert-butyl ester. [M+H]$^+$ 285.

Example 12

3,5-Diamino-6-chloro-pyrazine-2-carboxylic acid {(S)-2-amino-6-[2-(4-benzyloxy-phenyl)-acetylamino]-hexyl}-amide trifluororoacetate Step 1: ((S)-5-[2-(4-Benzyloxy-phenyl)-acetylamino]-1-{[(3,5-diamino-6-chloro-pyrazine-2-carbonyl)-amino]-methyl}-pentyl)-carbamic acid tert-butyl ester To a solution of 4-benzyloxy-phenyl-acetic acid (39 mg, 0.16 mmol) and HATU (61 mg, 0.16 mmol) in DMF (3 mL) is added N-methylmorpholine (64 mg, 0.64 mmol) followed by a solution of ((S)-5-amino-1-{[(3,5-diamino-6-chloro-pyrazine-2-carbonyl)-amino]-methyl}-pentyl)-carbamic acid tert-butyl ester (Intermediate C) (64 mg, 0.16 mmol) in DMF (2 mL). The resulting mixture is stirred at RT for 17 h. The solvent is removed in vacuo to afford the title compound which is used in the next step without further purification. [M+H]$^+$ 626.

Step 2: 3,5-Diamino-6-chloro-pyrazine-2-carboxylic acid {(S)-2-amino-6-[2-(4-benzyloxy-phenyl)-acetylamino]-hexyl}-amide trifluoroacetate A solution of ((S)-5-[2-(4-benzyloxy-phenyl)-acetylamino]-1-{[(3,5-diamino-6-chloro-pyrazine-2-carbonyl)-amino]-methyl}-pentyl)-carbamic acid tert-butyl ester (0.1 g, 0.16 mmol) in DCM (3 mL) and TFA (1 mL) is stirred at RT for 6 h. The solvent is removed in vacuo and the resulting residue is dissolved in DMSO and purified by reverse phase column chromatography (Isolute™ C18, 0-100% acetonitrile in water-0.1% TFA) to afford the title compound. [M+H]$^+$ 526. $^1$H NMR (500 MHz, DMSO-d6) δ 8.16 (1H, t), 8.05 (1H, t), 7.94 (4H, br), 7.42 (2H, d), 7.37 (2H, dd), 7.31 (1H, dd), 7.16 (2H, d), 7.04 (2H, br), 6.92 (2H, d), 5.05 (2H, s), 3.38 (2H, m), 3.31 (2H, s), 3.18 (1H, m), 3.02 (2H, m), 1.52 (2H, m), 1.38 (4H, m).

Example 13

3,5-Diamino-6-chloro-pyrazine-2-carboxylic acid ((S)-2-amino-hexyl)-amide hydrochloride The title compound is prepared by an analogous procedure to Example 4 by replacing ((S)-1-hydroxymethyl-butyl)-carbamic acid tert-butyl ester in Step 1 with ((S)-1-hydroxymethyl-pentyl)-carbamic acid tert-butyl ester. [M+H]$^+$ 287. ((S)-1-Hydroxymethyl-pentyl)-carbamic acid tert-butyl ester is prepared by an analogous procedure to 2-tert-butoxycarbonylamino-pent-4-enoic acid (Intermediate A, Step 1) by replacing allyl glycine with (S)-(+)-2-amino-1-hexanol.

Example 14

3,5-Diamino-6-chloro-pyrazine-2-carboxylic acid ((R)-2-amino-butyl)-amide hydrochloride The title compound is prepared by an analogous procedure to Example 4 by replacing ((S)-1-hydroxymethyl-butyl)-carbamic acid tert-butyl ester in step 1 with ((R)-1-hydroxymethyl-propyl)-carbamic acid tert-butyl ester. [M+H]$^+$ 259.

Example 15

3,5-Diamino-6-chloro-pyrazine-2-carboxylic acid ((R)-2-amino-propyl)-amide hydrochloride The title compound is prepared by an analogous procedure to Example 4 by replacing ((S)-1-hydroxymethyl-butyl)-carbamic acid tert-butyl ester in step 1 with ((R)-2-hydroxy-1-methyl-ethyl)-carbamic acid tert-butyl ester. [M+H]$^+$ 245.

Example 16

3,5-Diamino-6-chloro-pyrazine-2-carboxylic acid ((S)-2-amino-butyl)-amide hydrochloride The title compound is prepared by an analogous procedure to Example 4 by replacing ((S)-1-hydroxymethyl-butyl)-carbamic acid tert-butyl ester in step 1 with ((S)-1-hydroxymethyl-propyl)-carbamic acid tert-butyl ester. [M+H]$^+$ 259.

Example 17

3,5-Diamino-6-chloro-pyrazine-2-carboxylic acid ((S)-2-amino-propyl)-amide hydrochloride The title compound is prepared by an analogous procedure to Example 4 by replacing ((S)-1-hydroxymethyl-butyl)-carbamic acid tert-butyl ester in step 1 with ((S)-2-hydroxy-1-methyl-ethyl)-carbamic acid tert-butyl ester. [M+H]$^+$ 245.

Example 18

3,5-Diamino-6-chloro-pyrazine-2-carboxylic acid ((S)-1-piperidin-2-ylmethyl)-amide hydrochloride The title compound is prepared by an analogous procedure to Example 4 by replacing ((S)-1-aminomethyl-butyl)-carbamic acid tert-butyl ester in step 3 with (S)-2-aminomethyl-1-N-Boc-piperidine. [M+H]+ 285.

Example 19

3,5-Diamino-6-chloro-pyrazine-2-carboxylic acid ((R)-1-pyrrolidin-2-ylmethyl)-amide hydrochloride The title compound is prepared by an analogous procedure to Example 4 by replacing ((S)-1-aminomethyl-butyl)-carbamic acid tert-butyl ester in step 3 with (R)-2-aminomethyl-1-N-Boc-pyrrolidine. [M+H]+ 271.

Example 20

3,5-Diamino-6-chloro-pyrazine-2-carboxylic acid ((R)-2-amino-3-methyl-butyl)-amide hydrochloride The title compound is prepared by an analogous procedure to Example 4 by replacing ((S)-1-hydroxymethyl-butyl)-carbamic acid tert-butyl ester in step 1 with ((R)-1-hydroxymethyl-2-methyl-propyl)-carbamic acid tert-butyl ester. [M+H]+ 273.

Example 21

3,5-Diamino-6-chloro-pyrazine-2-carboxylic acid {(S)-2-amino-6-[3-(4-benzyloxy-phenyl)-propionylamino]-hexyl}-amide hydrochloride The title compound is prepared by an analogous procedure to Example 12 by replacing 4-benzyloxy-phenyl-acetic acid in step 1 with 3-(4-benzyloxyphenyl)propionoic acid. [M+H]+ 540.

Example 22

3,5-Diamino-6-chloro-pyrazine-2-carboxylic acid ((R)-2-guanidino-butyl)-amide trifluoroacetate A solution of N,N'-di-Boc-1H-pyrazole-1-carboxamidine (211 mg, 0.68 mmol), 3,5-diamino-6-chloro-pyrazine-2-carboxylic acid ((R)-2-amino-butyl)-amide (Example 14) (200 mg, 0.68 mmol) and triethylamine (0.20 ml, 1.43 mmol) in DMF (10 ml) is stirred at RT for 2 days. After this time the reaction mixture is concentrated in vacuo and the residue partitioned between EtOAc and saturated sodium hydrogen carbonate solution. The organic phase is washed with water, sat. aq. NaCl solution, dried over MgSO$_4$, and concentrated in vacuo. The crude material is dissolved in DCM (30 mL) and treated with excess TFA and stirred at RT for 4 days. The solvents are removed in vacuo and the residue is purified by reverse phase column chromatography (Isolute™ C18, 0-100% acetonitrile in water-0.1% TFA) to afford the title compound. [M+H]+ 301. $^1$H NMR (400 MHz, DMSO-d6) δ 8.04 (1H, t), 7.44 (1H, d), 7.37 (3H, br), 7.06 (2H, br), 6.81 (2H, br), 3.52-3.42 (1H, m), 3.40-3.31 (1H, m), 3.25-3.19 (1H, m), 1.64-1.53 (1H, m), 1.44-1.33 (1H, m), 0.89 (3H, t).

Example 23

3,5-Diamino-6-chloro-pyrazine-2-carboxylic acid ((S)-2-guanidino-pentyl)-amide trifluoroacetate The title compound is prepared by an analogous procedure to Example 23 by replacing 3,5-diamino-6-chloro-pyrazine-2-carboxylic acid ((R)-2-amino-butyl)-amide (Example 14) with 3,5-diamino-6-chloro-pyrazine-2-carboxylic acid ((S)-2-amino-pentyl)-amide hydrochloride (Example 4). [M+H]+ 315.

Example 24

3,5-Diamino-6-chloro-pyrazine-2-carboxylic acid ((R)-2-guanidino-pentyl)-amide trifluoroacetate The title compound is prepared by an analogous procedure to Example 23 by replacing 3,5-diamino-6-chloro-pyrazine-2-carboxylic acid ((R)-2-amino-butyl)-amide (Example 14) with 3,5-diamino-6-chloro-pyrazine-2-carboxylic acid ((R)-2-amino-pentyl)-amide hydrochloride (Example 5). [M+H]+ 315.

Example 25

3,5-Diamino-6-chloro-pyrazine-2-carboxylic acid ((S)-3-cyclohexyl-2-guanidino-propyl)-amide trifluoroacetate The title compound is prepared by an analogous procedure to Example 23 by replacing 3,5-diamino-6-chloro-pyrazine-2-carboxylic acid ((R)-2-amino-butyl)-amide (Example 14) with 3,5-diamino-6-chloro-pyrazine-2-carboxylic acid ((S)-2-amino-3-cyclohexyl-propyl)-amide hydrochloride (Example 6). [M+H]+ 369.

Example 26

3,5-Diamino-6-chloro-pyrazine-2-carboxylic acid {(S)-2-[3-(4-methoxy-phenyl)-propylamino]-pentyl}-amide hydrochloride A solution of 3,5-Diamino-6-chloro-pyrazine-2-carboxylic acid ((S)-2-amino-pentyl)-amide hydrochloride (Example 4) (400 mg, 1.467 mmol), 3-(4-methoxyphenyl)propionaldehyde (181 mg, 1.103 mmol) and sodium triacetoxyborohydride (467 mg, 2.205 mmol) in DCM (150 mL) is heated at reflux overnight. The reaction mixture is allowed to cool, and 1 N NaOH solution (50 mL) and DCM (50 mL) are added. The organic phase is separated and the aqueous phase is extracted once with DCM. The combined organic phases are washed with sat. aq. NaCl solution, dried (MgSO$_4$), and concentrated in vacuo to afford a yellow solid. Purification by flash column chromatography (SiO$_2$, MeOH:DCM, gradient 2-10%+0.1% TEA) affords the title compound. [M+H]+ 421. $^1$H NMR (400 MHz, CDCl$_3$) δ 8.69 (2H, br), 8.23 (1H, t), 7.25 (4H, br), 7.11 (2H, d), 6.84 (2H, d), 3.72 (3H, s), 3.55-3.45 (2H, m), 3.25-3.15 (1H, m), 3.03-2.92 (2H, m), 2.58 (2H, t), 1.85-1.73 (2H, m), 1.65-1.27 (4H, m), 0.89 (3H, t).

Example 27

3,5-Diamino-6-chloro-pyrazine-2-carboxylic acid {(S)-6-[2-(4-benzyloxy-phenyl)-acetylamino]-2-guanidino-hexyl}-amide trifluoroacetate The title compound is prepared by an analogous procedure to Example 23 by replacing 3,5-diamino-6-chloro-pyrazine-2-carboxylic acid ((R)-2-amino-butyl)-amide (Example 14) with 3,5-diamino-6-chloro-pyrazine-2-carboxylic acid {(S)-2-amino-6-[2-(4-benzyloxy-phenyl)-acetylamino]-hexyl}-amide (Example 22). [M+H]+ 568.

Example 28

3,5-Diamino-6-chloro-pyrazine-2-carboxylic acid ((S)-2-{N-[3-(4-methoxy-phenyl)-propyl]-guanidino}-pentyl)-amide hydrochloride To a solution of N,N'-Di-Boc-thiourea (342 mg, 1.237 mmol) in anhydrous DCM (50 mL) is added 3,5-diamino-6-chloro-pyrazine-2-carboxylic acid {(S)-2-[3-(4-methoxyphenyl)-propylamino]-pentyl}-amide hydrochloride (Example 27) (347 mg, 0.824 mmol) and polymer supported CDI (1.74 g, 2.473 mmol). The reaction mixture is stirred at RT for 6 h. The resin is removed by filtration and washed with DCM (20 mL). To the combined filtrates is added polymer supported Trisamine (602 mg, 1.65 mmol) and the reaction is stirred at RT for 1 h. Filtration removed the resin, which is washed with DCM (10 mL). The combined filtrates are concentrated in vacuo and purified by flash column chromatography (SiO$_2$, 2% MeOH in DCM) to afford a pale yellow oil. The oil is dissolved in DCM (200 mL) and a solution of 4 M HCl in 1,4-dioxane (10 mL) is added, and the solution is stirred at RT overnight. The reaction mixture is concentrated in vacuo and purification by reverse phase column chromatography (Isolute™ C18, 0-100% acetonitrile in water-0.1% TFA) affords the title compound. [M+H]$^+$ 463. $^1$H NMR (500 MHz, DMSO-d6) δ 8.04 (1H, br), 7.44 (4H, br), 7.34-6.88 (4H, br), 7.11 (2H, d), 6.83 (2H, d), 6.10-4.30 (3H, br), 3.92 (1H, m), 3.71 (3H, s), 3.49-3.48 (1H, m), 3.42-3.3.14 (3H, m), 2.55-2.48 (2H, m), 1.80-1.61 (2H, m), 1.51-1.48 (2H, m), 1.27-1.1.15 (2H, m), 0.84 (3H, t).

Example 29

3,5-Diamino-6-chloro-pyrazine-2-carboxylic acid ((R)-2-{N-[3-(4-methoxy-phenyl)-propyl]-guanidino}-pentyl)-amide trifluoroacetate The title compound is prepared by an analogous procedure to Example 29 by replacing 3,5-diamino-6-chloro-pyrazine-2-carboxylic acid {(S)-2-[3-(4-methoxy-phenyl)-propylamino]-pentyl}-amide hydrochloride (Example 27) with 3,5-diamino-6-chloro-pyrazine-2-carboxylic acid {(R)-2-[3-(4-methoxy-phenyl)-propylamino]-pentyl}-amide hydrochloride (Intermediate D). [M+H]$^+$ 463.

Example 30

3,5-Diamino-6-chloro-pyrazine-2-carboxylic acid [(S)-2-(N-{3-[4-((S)-2,3-dihydroxy-propoxy)-phenyl]-propyl}-guanidino)-pentyl]-amide hydrochloride

Step 1: 3-[4-((R)-2,2-Dimethyl-[1,3]-dioxolan-4-ylmethoxy)-phenyl]-propionaldehyde To (3-[4-((R)-2,2-dimethyl-[1,3]-dioxolan-4-ylmethoxy)-phenyl]-propan-1-ol (Intermediate B, Step 2) (1.18 g, 4.42 mmol) in DCM (150 mL) is added Dess-Martin periodinane (1.88 g, 4.42 mmol). The reaction mixture is stirred at RT for 3 h then treated with 1 N NaOH solution (50 mL) and stirred at RT for 1 h. The organic layer is separated, dried (MgSO$_4$), filtered and concentrated in vacuo to give a clear oil. Purification by flash column chromatography (SiO$_2$, EtOAc:iso-hexane, gradient 17-25%) affords the title compound. [M+H]$^+$ 265.

Step 2: 3,5-Diamino-6-chloro-pyrazine-2-carboxylic acid ((S)-2-{3-[4-((R)-2,2-dimethyl-[1,3]-dioxolan-4-lmethoxy)-phenyl]-propylamino}-pentyl)-amide The title compound is prepared by an analogous procedure to Example 27 by replacing 3-(4-methoxyphenyl)propionaldehyde with 3-[4-((R)-2,2-dimethyl-[1,3]-dioxolan-4-ylmethoxy)-phenyl]-propionaldehyde. [M+H]$^+$ 521.

Step 3: 3,5-Diamino-6-chloro-pyrazine-2-carboxylic acid [(S)-2-(N-{3-[4-((S)-2,3-dihydroxy-propoxy)-phenyl]-propyl}-guanidino)-pentyl]-amide hydrochloride The title compound is prepared by an analogous procedure to Example 29 by replacing 3,5-diamino-6-chloro-pyrazine-2-carboxylic acid {(S)-2-[3-(4-methoxy-phenyl)-propylamino]-pentyl}-amide hydrochloride (Example 27) with 3,5-diamino-6-chloro-pyrazine-2-carboxylic acid ((S)-2-{3-[4-((R)-2,2-dimethyl-[1,3]-dioxolan-4-ylmethoxy)-phenyl]-propylamino}-pentyl)-amide. [M+H]$^+$ 523. $^1$H NMR (400 MHz, DMSO-d6) δ 8.04 (1H, t), 7.36 (2H, br), 7.34 (2H, s), 7.11 (2H, d), 7.05 (2H, br), 6.84 (2H, d), 5.78 (3H, br), 3.97-3.91 (2H, m), 3.83-3.74 (2H, m), 3.49-3.34 (3H, m), 3.35-3.10 (3H, m), 2.51 (2H, t), 1.81-1.58 (2H, m), 1.51-1.48 (2H, m), 1.25-1.10 (2H, m), 0.85 (3H, t).

Example 31

3,5-Diamino-6-chloro-pyrazine-2-carboxylic acid ((S)-2-{N'-[3-(4-methoxy-phenyl)-propyl]-guanidino}-pentyl)-amide

Step 1: (S,E)-tert-butyl 1-(3,5-diamino-6-chloropyrazin-2-yl)-7-(3-(4-methoxyphenyl)propyl)-10,10-dimethyl-1,8-dioxo-4-propyl-9-oxa-2,5,7-triazaundecan-6-ylidenecarbamate To a stirred solution of 3,5-Diamino-6-chloro-pyrazine-2-carboxylic acid ((S)-2-amino-pentyl)-amide hydrochloride (Example 4) (0.2 g, 0.73 mmol) in DMF (3 mL) is added triethylamine (0.22 mL, 1.54 mmol) followed by {[(Z)-tert-Butoxycarbonylimino]-pyrazol-1-yl-methyl}-[3-(4-methoxy-phenyl)-propyl]-carbamic acid tert-butyl ester (Intermediate E) and the resulting deep yellow solution is stirred at RT for 3 days. The reaction mixture is diluted with water (50 mL) and extracted with EtOAc (100 mL). The organic phase is washed with water (50 ml), dried (MgSO$_4$), and the solvent removed in vacuo to afford a yellow oil. Chromatography (SiO$_2$, EtOAc:iso-hexane, gradient 0-100%) affords (S,E)-tert-butyl 1-(3,5-diamino-6-chloropyrazin-2-yl)-7-(3-(4-methoxyphenyl)propyl)-10,10-dimethyl-1,8-dioxo-4-propyl-9-oxa-2,5,7-triazaundecan-6-ylidenecarbamate as a colourless oil. [M+H]$^+$ 663.

Step 2: 3,5-Diamino-6-chloro-pyrazine-2-carboxylic acid ((S)-2-{N'-[3-(4-methoxy-phenyl)-propyl]-guanidino}-pentyl)-amide A solution of 4N HCl in 1,4-dioxane (5 mL) is added to a solution of (S,E)-tert-butyl 1-(3,5-diamino-6-chloropyrazin-2-yl)-7-(3-(4-methoxyphenyl)propyl)-10,10-dimethyl-1,8-dioxo-4-propyl-9-oxa-2,5,7-triazaundecan-6-ylidenecarbamate (0.14 g, 0.21 mmol) in 1,4-dioxane (5 mL) and the resulting yellow solution is stirred at RT overnight.

Diethyl ether (20 mL) is added and an orange gum precipitates out of solution. The solvent is decanted off, and the gum is washed with diethyl ether (2×15 mL), and dried in vacuo at 40° C. The solid is dissolved in a 1:1 mixture of 2N NaOH and EtOAc. The organic phase is separated, dried over MgSO$_4$, and the solvent removed in vacuo to afford a yellow oil. Et$_2$O (10 mL) is added and the solvent removed in vacuo to afford a yellow foam which is dried in vacuo at 40° C. for 15 hours to afford the title compound. [M+H]$^+$ 463. $^1$H NMR (400 MHz, DMSO-d6) δ 7.10 (2H, d), 7.00 (2H, br s), 6.82 (2H, d), 3.71 (3H, s), 3.55-3.45 (1H, m), 3.45-3.10 (2H, m), 3.03 (2H, t), 2.54 (2H, m), 1.72 (2H, t), 1.50-1.20 (4H, m), 0.85 (3H, t).

Example 32

3,5-Diamino-6-chloro-pyrazine-2-carboxylic acid {(S)-2-[N'-(4-methoxy-benzyl)-guanidino]-pentyl}-amide The title compound is prepared by an analogous procedure to Example 32 by replacing {[(Z)-tert-Butoxycarbonylimino]-pyrazol-1-yl-methyl}-[3-(4-methoxy-phenyl)-propyl]-carbamic acid tert-butyl ester (Intermediate E) in step 1 with {[(E)-tert-Butoxycarbonylimino]-pyrazol-1-yl-methyl}-(4-methoxy-benzyl)-carbamic acid tert-butyl ester (Intermediate F). [M+H]$^+$ 435.

Example 33

3,5-Diamino-6-chloro-pyrazine-2-carboxylic acid {(R)-2-[N'-(4-methoxy-benzyl)-guanidino]-pentyl}-amide The title compound is prepared by an analogous procedure to Example 33 by replacing 3,5-Diamino-6-chloro-pyrazine-2-carboxylic acid ((S)-2-amino-pentyl)-amide hydrochloride (Example 4) in step 1 with 3,5-Diamino-6-chloro-pyrazine-2-carboxylic acid ((R)-2-amino-pentyl)-amide hydrochloride (Example 5). [M+H]$^+$ 435.

Preparation of Intermediate Compounds

Intermediate A 2-(tert-Butoxymethyl-amino)-5-(4-methoxy-phenyl)-pentanoic acid amide Step 1: 2-tert-Butoxycarbonylamino-pent-4-enoic acid A suspension of allyl glycine (5.0 g, 43.4 mmol) in dry DCM (60 mL) is treated with triethylamine (9 mL, 69.4 mmol) and cooled to 0° C. To this mixture is added a cooled solution of di-tent-butyl dicarbonate (12.3 g, 56.7 mmol) in dry DCM (30 mL) and the resulting mixture is allowed to warm to RT and stirred for 3 days. The mixture is washed twice with 2M HCl$_{(aq)}$ and the organic portion is separated, dried (MgSO$_4$) and concentrated in vacuo to afford the title compound as a light-green oil which is used in the next step without further purification.

Step 2: 2-tert-Butoxycarbonylamino-pent-4-enoic acid methyl ester 2-tert-Butoxycarbonylamino-pent-4-enoic acid (9.3 g, 43.3 mmol) in acetone (70 mL) is treated with solid potassium carbonate (11.9 g, 86.6 mmol) followed by methyl iodide (5.4 mL, 86.6 mmol). The resulting mixture is heated to reflux for 4 h and then allowed to cool to RT. The solvent is removed in vacuo and the crude residue is dissolved in EtOAc, washed with water, saturated sodium hydrogen carbonate solution, brine, dried (MgSO$_4$) and concentrated in vacuo. The crude residue is purified by flash chromatography (SiO$_2$, iso-hexane:EtOAc 7:3) to afford the title compound as a light-yellow oil.

Step 3: 2-tert-Butoxycarbonylamino-5-(4-methoxy-phenyl)-pentanoic acid methyl ester To a cooled (0° C.) mixture comprising 2-tert-butoxycarbonylamino-pent-4-enoic acid methyl ester (4.0 g, 17.46 mmol) in dry THF (60 mL) under an inert atmosphere of argon is added 9-BBN (70 mL of a 0.5 M solution in THF, 35.0 mmol). The reaction is stirred at RT for 2 h. To this mixture is added degassed DMF (50 mL) followed by an aqueous solution of potassium phosphate (12 mL of a 3 M aqueous solution, 36 mmol). 4-Iodoanisole (4.3 g, 18.8 mmol) is added immediately followed by PdCl$_2$(dppf) (0.63 g, 0.86 mmol) and the mixture is stirred at RT overnight. The solvent is removed in vacuo and the crude residue is dissolved in EtOAc and filtered through Celite® (filter material). The filtrate is washed with saturated sodium hydrogen carbonate solution, water (×3), brine, and then dried (MgSO$_4$) and concentrated in vacuo. Purification of the crude product by flash chromatography (SiO$_2$, iso-hexane:EtOAc, 9:1) affords the title compound as a light brown oil.

Step 4: [1-Carbamoyl-4-(4-methoxy-phenyl)-butyl]-carbamic acid tert-butyl ester

A solution of 2-tert-butoxycarbonylamino-5-(4-methoxy-phenyl)-pentanoic acid methyl ester (5.6 g, 16.6 mmol) in MeOH (100 mL) is treated with aqueous ammonia solution (100 mL of a 28% solution in water, 28 mmol) and stirred at RT overnight. The organic solvent is removed in vacuo and the remaining aqueous portion is extracted with EtOAc (×3). The combined organic extracts are washed with brine and then dried (MgSO$_4$) and concentrated in vacuo to afford the title compound as a yellow oil.

Step 5: [1-Aminomethyl-4-(4-methoxy-phenyl)-butyl]-carbamic acid tert-butyl ester A solution of [1-carbamoyl-4-(4-methoxy-phenyl)-butyl]-carbamic acid tert-butyl ester (0.5 g, 1.48 mmol) in THF (15 mL) is treated dropwise with 1M borane-THF complex (4.47 mL, 4.47 mmol) and then heated at reflux for 2 h. After cooling to RT, MeOH (20 mL) is added and the mixture is heated again at reflux for 2 h. The solvent is removed in vacuo and the resulting oil is dissolved in DCM (10 mL) and filtered through Celite® (filter material). The filtrate is concentrated in vacuo to afford the title compound as a colourless oil. [M+H]$^+$ 308.

Intermediate B

2-Amino-5-[4-((R)-2,2-dimethyl-[1,3]dioxolan-4-ylmethoxy)-phenyl]-pentanenitrile Step 1: (S)-3-[4-(3-Hydroxy-propyl)-phenoxy]-propane-1,2-diol To 3-(4-hydroxyphenyl)-1-propanol (10.0 g, 66.0 mmol) and potassium carbonate (13.5 g, 100 mmol) in acetone (200 mL) is added (S)-glycidol (6.5 mL, 100 mmol). The mixture is heated at reflux for 18 h. After cooling to RT the solvent is removed in vacuo and the residue partitioned between EtOAc and water. The aqueous layer is further extracted twice with EtOAc and the combined organic portions are washed with water, brine, then dried (MgSO$_4$), filtered and concentrated in vacuo. The crude residue is purified by flash chromatography (SiO$_2$, EtOAc:iso-hexane, 1:1) to afford the title compound as a white solid.

Step 2: (3-[4-((R)-2,2-Dimethyl-[1,3]dioxolan-4-ylmethoxy)-phenyl]-propan-1-ol To (S)-3-[4-(3-hydroxy-propyl)-phenoxy]-propane-1,2-diol (11.5 g, 50.9 mmol) in dry DMF (150 mL) is added pyridinium p-toluenesulfonate (1.28 g, 5.0 mmol) and 2,2-dimethoxypropane (31 mL, 250 mmol). The mixture is stirred at RT for 18 h and then the solvent is removed in vacuo. The residue is dissolved in EtOAc (150 mL) and washed with water, saturated aqueous sodium hydrogen carbonate solution, brine, dried (MgSO$_4$) and concentrated in vacuo. The residue is purified by flash chromatography (SiO$_2$, EtOAc: iso-hexane, gradient 20% to 50% EtOAc) to afford the title compound as a colourless oil.

Step 3: Methanesulfonic acid 3-[4-((R)-2,2-dimethyl [1,3]dioxolan-4-ylmethoxy)-phenyl]-propylester To (3-[4-((R)-2,2-dimethyl-[1,3]dioxolan-4-ylmethoxy)-phenyl]-propan-1-ol (12.2 g, 46 mmol) in dry diethyl ether (150 mL) is added triethylamine (12.8 mL, 92 mmol). The mixture is cooled to 0° C. and treated dropwise with methanesulfonyl chloride (5.3 mL, 69 mmol). The reaction mixture is allowed to warm to RT and then stirring is continued for 3 h. The resulting mixture is washed with water (2×100 mL), saturated aqueous sodium hydrogen carbonate solution, brine then dried (MgSO$_4$) and concentrated in vacuo to give the title compound as a white solid.

Step 4: (R)-4-[4-(3-Bromo-propyl)-phenoxymethyl]-2,2-dimethyl-[1,3]dioxolane Methanesulfonic acid 3-[4-((R)-2,2-dimethyl[1,3]dioxolan-4-ylmethoxy)-phenyl]-propylester (11.8 g, 34.2 mmol) in acetone (200 mL) is treated with lithium bromide (8.9 g, 100 mmol) and then heated to reflux for 5 h. After cooling to RT the mixture is concentrated in vacuo. The resulting residue is dissolved in EtOAc (150 mL), washed with water (2×50 mL), brine then dried (MgSO$_4$), filtered and concentrated in vacuo to give an oil. Purification by flash chromatography (SiO$_2$, iso-hexane:EtOAc, 4:1) gives the title compound as colourless oil that solidifies upon standing.

Step 5: 2-(Benzhydrylidene-amino)-5-[4-((R)-2,2-dimethyl-[1,3]-dioxolan-4-ylmethoxy)-phenyl]pentanenitrile A solution of N-(diphenylmethylene) aminoacetonitrile (5.14 g, 23.4 mmol) in DCM (12 mL) is treated with (R)-4-[4-(3-bromo-propyl)-phenoxymethyl]-2,2-dimethyl-[1,3]dioxolane (8.1 g, 24 mmol) in DCM (12 mL) and cooled to 0° C. Aqueous NaOH (20 mL of a 48% aqueous solution) is added followed by benzyltriethylammonium chloride (530 mg, 2.4 mmol) and the resulting mixture is allowed to warm to RT. After stirring vigorously for 4 h the mixture is diluted with DCM (100 mL) and the aqueous portion is removed. The organic layer is washed with water (2×50 mL), brine then dried (MgSO$_4$), filtered and concentrated in vacuo. The crude product is purified by flash chromatography (SiO$_2$, iso-hexane:diethyl ether) to yield the title compound as yellow oil as a mixture of diastereoisomers.

Step 6: 2-Amino-5-[4-((R)-2,2-dimethyl-[1,3]-dioxolan-4-ylmethoxy)-phenyl]-pentanenitrile To a solution of 2-(benzhydrylidene-amino)-5-[4-((R)-2,2-dimethyl-[1,3]-dioxolan-4-ylmethoxy)-phenyl]pentanenitrile (7.2 g, 15.5 mmol) in THF (50 mL) is added aqueous HCl (5 mL of a 2 M solution). The solution is heated at 40° C. for 4 h and then allowed to cool to RT. The pH is adjusted to 9-10 using saturated aqueous sodium hydrogen carbonate solution and the organic solvent is removed in vacuo. The crude residue is dissolved in EtOAc (100 mL) and washed with water, brine then dried (MgSO$_4$), filtered and concentrated in vacuo. The resulting residue is purified by chromatography (SiO$_2$, iso-hexane:EtOAc with 1% triethylamine) to yield the title compound as colourless oil that solidifies upon standing as a mixture of diastereoisomers. [M+H]$^+$ 305.

Intermediate C ((S)-5-Amino-1-{[(3,5-diamino-6-chloro-pyrazine-2-carbonyl)-amino]-methyl}-pentyl)-carbamic acid tert-butyl ester

Step 1: ((S)-5-Benzyloxycarbonylamino-1-{[(3,5-diamino-6-chloro-pyrazine-2-carbonyl)-amino]-methyl}-pentyl)-carbamic acid tert-butyl ester To a solution of 3,5-diamino-6-chloro-pyrazine-2-carboxylic acid (386 mg, 2.05 mmol) and HATU (781 mg, 2.05 mmol) in DMF (10 mL) is added N-methyl morpholine (831 mg, 8.22 mmol) followed by ((S)-1-aminomethyl-5-benzyloxycarbonylamino-pentyl)-carbamic acid tert-butyl ester (prepared according to the procedure described in WO1997/01204 page 20) (750 mg, 2.05 mmol). The resulting solution is stirred at RT for 18 h and then concentrated in vacuo to afford an orange oil. The oil is dissolved in MeOH (10 mL) and allowed to stand at RT after which time a cream precipitate forms that is collected by filtration and dried under vacuum to yield the title compound. [M+H]$^+$ 536.

Step 2: ((S)-5-Amino-1-{[(3,5-diamino-6-chloro-pyrazine-2-carbonyl)-amino]-methyl}-pentyl)-carbamic acid tert-butyl ester A suspension of ((S)-5-benzyloxycarbonylamino-1-{[(3,5-diamino-6-chloro-pyrazine-2-carbonyl)-amino]-methyl}-pentyl)-carbamic acid tert-butyl ester (680 mg, 1.27 mmol) in EtOH (20 mL) under an inert atmosphere of N2 is treated with activated palladium on charcoal (10%). The reaction mixture is then placed under a positive pressure of hydrogen and stirred at RT. After 3 h, the mixture is purged with N2 and the catalyst is removed by filtration through Celite® (filter material). The filtrate is concentrated in vacuo and the resulting colourless oil is dissolved in MeOH (10 mL) and allowed to stand at RT overnight. The cream precipitate which forms is removed by filtration and the solution is concentrated in vacuo. The resulting crude product is purified by reverse phase column chromatography (Isolute™ C18, 0-100% acetonitrile in water with 0.1% NH$_3$) to afford the title compound. [M+H]$^+$ 402.

Intermediate D 3,5-Diamino-6-chloro-pyrazine-2-carboxylic acid {(R)-2-[3-(4-methoxy-phenyl)-propylamino]-pentyl}-amide hydrochloride The title compound is prepared by an analogous procedure to Example 27 by replacing 3,5-diamino-6-chloro-pyrazine- 2-carboxylic acid ((S)-2-amino-pentyl)-amide hydrochloride (Example 4) with 3,5-diamino-6-chloro-pyrazine-2-carboxylic acid ((R)-2-amino-pentyl)-amide hydrochloride (Example 5). [M+H]⁺ 421.

Intermediate E

{[(Z)-tert-Butoxycarbonylimino]-pyrazol-1-yl-methyl}-[3-(4-methoxy-phenyl)-propyl]-carbamic acid tert-butyl ester PS-Triphenylphosphine (6.40 g, 12.03 mmol) is added to a solution of 3-(4-methoxyphenyl)-1-propanol (1.00 g, 6.02 mmol) in DCM (300 mL), followed by N,N'-di-Boc-1H-pyrazole-1-carboxamidine (1.87 g, 6.02 mmol). The reaction mixture is cooled to 4° C., and di-tert-butyl azodicarboxylate (1.39 g, 6.02 mmol) is added portionwise. The reaction is stirred for 5 minutes at 4° C., and then allowed to warm to RT. The resulting yellow suspension is stirred at RT overnight. The reaction is filtered to remove the PS-triphenylphosphine, which is rinsed with MeOH (20 mL). The combined filtrates are concentrated in vacuo to afford a colourless oil. iso-Hexane (50 mL) is added, and a fine cream solid precipitates out of solution, which is removed by filtration. The filtrate is concentrated in vacuo, and the resulting white solid is washed with iso-hexane (50 mL). The iso-hexane is concentrated in vacuo, and the resulting pale yellow oil is purified by chromatography (SiO₂, EtOAc in iso-hexane, 0%-25%) to afford the title compound crude as a colourless oil. The oil is used in further reactions with no further purification. [M+H]⁺ 459.

Intermediate F

{[(E)-tert-Butoxycarbonylimino]-pyrazol-1-yl-methyl}-(4-methoxy-benzyl)-carbamic acid tert-butyl ester The title compound is prepared by an analogous procedure to Intermediate E by replacing 3-(4-methoxyphenyl)-1-propanol with 4-methoxybenzylalcohol. [M+H]⁺ 431.

The invention claimed is:

1. A compound which is selected from:
3,5-Diamino-6-chloro-pyrazine-2-carboxylic acid ((S)-2-amino-pentyl) -amide, 3,5-Diamino-6-chloro-pyrazine-2-carboxylic acid ((R)-2-amino-pentyl)-amide, 3,5-Diamino-6-chloro-pyrazine-2-carboxylic acid ((S)-2-amino-3-cyclohexyl-propyl)-amide, 3,5-Diamino-6-chloro-pyrazine-2-carboxylic acid ((S)-2-amino-3-methyl-butyl)-amide, 3,5-Diamino-6-chloro-pyrazine-2-carboxylic acid ((S)-2-amino-4-methyl-pentyl)-amide, 3,5-Diamino-6-chloro-pyrazine-2-carboxylic acid ((S)-2-amino-hexyl)-amide, 3,5-Diamino-6-chloro-pyrazine-2-carboxylic acid ((R)-2-amino-butyl)-amide, 3,5-Diamino-6-chloro-pyrazine-2-carboxylic acid ((R)-2-amino-propyl)-amide, 3,5-Diamino-6-chloro-pyrazine-2-carboxylic acid ((S)-2-amino-butyl)-amide, 3,5-Diamino-6-chloro-pyrazine-2-carboxylic acid ((S)-2-amino-propyl)-amide, or a pharmaceutically acceptable salt thereof.

2. The compound of claim 1, which is a pharmaceutically acceptable salt.

3. A pharmaceutical composition, comprising:
the compound of claim 1, together with at least one pharmaceutically acceptable carrier, diluent or excipient.

\* \* \* \* \*